(12) United States Patent
Zhang et al.

(10) Patent No.: US 11,891,405 B2
(45) Date of Patent: Feb. 6, 2024

(54) FURO[3,4-B]PYRROLE-CONTAINING BTK INHIBITOR

(71) Applicant: CHIA TAI TIANQING PHARMACEUTICAL GROUP CO., LTD., Lianyungang (CN)

(72) Inventors: Yinsheng Zhang, Lianyungang (CN); Hongjiang Xu, Lianyungang (CN); Jing Ren, Lianyungang (CN); Qinglin Wang, Lianyungang (CN); Zheyang Wu, Lianyungang (CN); Chao Jin, Lianyungang (CN); Wei Shi, Lianyungang (CN); Xiaojin Wang, Lianyungang (CN); Xiangyi He, Lianyungang (CN); Xiayun Chang, Lianyungang (CN); Jie Wang, Lianyungang (CN); Tianxiao Zhao, Lianyungang (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 524 days.

(21) Appl. No.: 17/276,025

(22) PCT Filed: Sep. 12, 2019

(86) PCT No.: PCT/CN2019/105584
§ 371 (c)(1),
(2) Date: Mar. 12, 2021

(87) PCT Pub. No.: WO2020/052628
PCT Pub. Date: Mar. 19, 2020

(65) Prior Publication Data
US 2022/0033419 A1    Feb. 3, 2022

(30) Foreign Application Priority Data
Sep. 14, 2018 (CN) .......................... 201811072116.0

(51) Int. Cl.
*C07D 519/00* (2006.01)

(52) U.S. Cl.
CPC .................................. *C07D 519/00* (2013.01)

(58) Field of Classification Search
CPC .................................................... C07D 519/00
USPC ........................................................ 514/249
See application file for complete search history.

(56) References Cited

U.S. PATENT DOCUMENTS

2019/0211023 A1   7/2019  Yin et al.
2019/0315758 A1   10/2019 Li et al.

FOREIGN PATENT DOCUMENTS

| CN | 108129483 | 6/2016 |
|---|---|---|
| CN | 106831789 | 6/2017 |
| CN | 107556317 | 1/2018 |
| CN | 107759602 | 3/2018 |
| WO | WO 2017/077507 | 5/2017 |
| WO | WO2018133151 | 7/2018 |
| WO | WO 2020/052628 | 3/2020 |

OTHER PUBLICATIONS

PCT International Search Report and Written Opinion in International Appln. No. PCT/CN2019/105584, dated Nov. 21, 2019, 2 pages.
Wuts et al., Greene's Protective Groups In Organic Synthesis, 4th ed., Apr. 2006, 1264 Pages.
Extended European Search Report in European Appln No. 19861061. 0, dated May 11, 2022, 6 pages.

*Primary Examiner* — Kristin A Vajda
(74) *Attorney, Agent, or Firm* — Fish & Richardson P.C.

(57) ABSTRACT

The present application belongs to the field of pharmaceutical chemistry, and relates to a furo[3,4-b]pyrrole-containing BTK inhibitor, and in particular, to a compound of formula (I), a stereisomer or pharmacologically acceptable salt thereof, a preparation method therefor, a pharmaceutical composition containing the compound, and use thereof in treating BTK-related diseases.

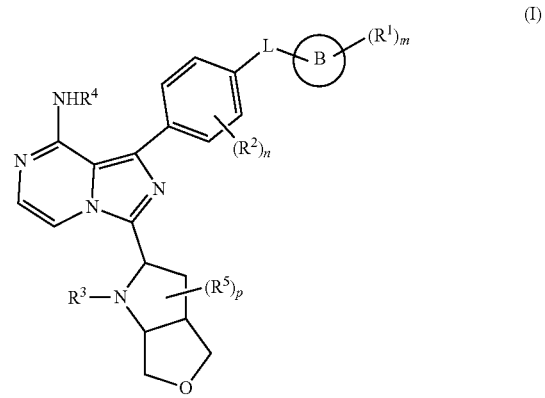

(I)

20 Claims, No Drawings

FURO[3,4-B]PYRROLE-CONTAINING BTK INHIBITOR

CROSS-REFERENCE TO RELATED APPLICATIONS

The present application claims priority and benefit to the Chinese Patent Application No. 201811072116.0, filed with National Intellectual Property Administration, PRC on Sep. 14, 2018, the disclosure of which is incorporated herein by reference in its entirety.

TECHNICAL FIELD

The present application relates to a furo[3,4-b]pyrrole-containing compound as a BTK inhibitor, a method for preparing the same, a pharmaceutical composition containing the same, and use of the same in treating a BTK related disease.

BACKGROUND

Bruton's Tyrosine Kinase (BTK) is mainly expressed in B cells and distributed in the lymphatic system and hematopoietic and blood system. BTK is a member of non-receptor tyrosine kinase Tec family, which also includes TEC, ITK/TSK/EMT and BMX that are highly homogeneous in structure. BTK plays a crucial role in B-cell signaling pathway that connects B-cell receptor stimulation on cell surface to downstream intracellular response, and is a key regulator of the development, activation, signaling and survival of B cells. In recent years, researches on B cells, particularly on B-cell non-Hodgkin's lymphoma and rheumatoid arthritis have found that BTK tends to be abnormally expressed.

Small-molecule targeted drugs are developed based on the BTK signaling pathway, providing a brand new approach for the treatment of B-cell tumors such as leukemia, multiple myeloma and B-cell immune diseases.

Currently, irreversible inhibitors such as ibrutinib on the market often have mutations in their BTK binding sites, which lead to decreased pharmaceutical activity, and thus resulting in drug resistance. Therefore, more BTK inhibitors are clinically needed, and they should have higher selectivity for BTK, so as to avoid toxic and side effects caused by off-target effect.

BRIEF SUMMARY

In one aspect, the present application provides a compound of formula (I), a stereoisomer thereof or a pharmaceutically acceptable salt thereof,

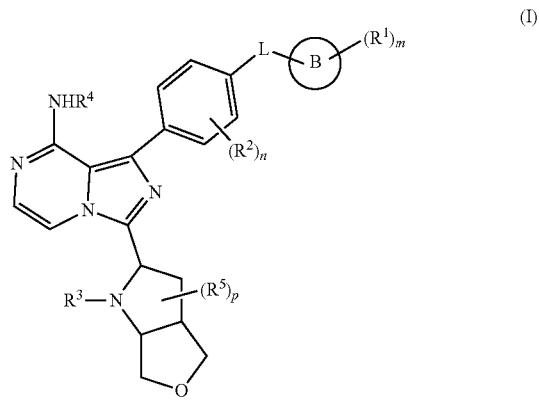

(I)

wherein, ring B is selected from the group consisting of 5-10 membered heteroaryl and $C_{6-10}$ aryl;

$R^1$ is independently selected from the group consisting of halogen, —OH, —NH$_2$, cyano, $C_{1-6}$ alkyl and $C_{1-6}$ alkoxy, wherein the $C_{1-6}$ alkyl and $C_{1-6}$ alkoxy is optionally substituted with halogen;

m is selected from the group consisting of 0, 1, 2, 3 and 4;

L is selected from the group consisting of —C(O)NH—, —NHC(O)—, —O—, —NH—, —S—, —C(O)O—, —OC(O)—, —S(O)$_2$O— and —OS(O)$_2$—;

$R^2$ is independently selected from the group consisting of halogen, —OH, —NH$_2$, cyano, $C_{1-6}$ alkyl and $C_{1-6}$ alkoxy, wherein the $C_{1-6}$ alkyl and $C_{1-6}$ alkoxy is optionally substituted with halogen;

n is selected from the group consisting of 0, 1, 2, 3 and 4;

$R^3$ is selected from the group consisting of H, $R^aC(O)$—, $R^aS(O)_2$— and $R^a$—;

$R^5$ is independently selected from the group consisting of halogen, —OH, —NH$_2$, cyano, $C_{1-6}$ alkyl and $C_{1-6}$ alkoxy;

p is selected from the group consisting of 0, 1, 2 and 3;

$R^4$ is selected from the group consisting of hydrogen, $R^aS(O)_2$—, $(R^aO)_2P(O)$— and $R^aC(O)$—;

wherein $R^a$ is independently selected from the group consisting of $C_{2-6}$ alkynyl, $C_{2-6}$ alkenyl, $C_{1-6}$ alkyl, $C_{3-6}$ cycloalkyl, ($C_{1-6}$ alkyl)NH—, ($C_{1-6}$ alkyl)$_2$N—, 3-6 membered heterocycloalkyl, 5-10 membered heteroaryl and $C_{6-10}$ aryl, wherein the $R^a$ is optionally substituted with ($C_{1-6}$ alkyl)$_2$N—, ($C_{1-6}$ alkyl)NH—, hydroxy, amino, halogen or cyano.

In another aspect, the present application provides a pharmaceutical composition comprising the compound of formula (I), the stereoisomer thereof or the pharmaceutically acceptable salt thereof.

In another aspect, the present application provides a method for preventing or treating a BTK-related disease in a mammal, comprising administering to the mammal in need of such treatment a therapeutically effective amount of the compound of formula (I), the stereoisomer thereof or the pharmaceutically acceptable salt thereof, or the pharmaceutical composition thereof.

In yet another aspect, the present application provides the use of the compound of formula (I), the stereoisomer thereof or the pharmaceutically acceptable salt thereof, or the pharmaceutical composition thereof in preparing a medicament for preventing or treating a BTK-related disease.

In yet another aspect, the present application provides use of the compound of formula (I), the stereoisomer thereof or the pharmaceutically acceptable salt thereof, or the pharmaceutical composition thereof in preventing or treating a BTK-related disease.

In yet another aspect, the present application provides the compound of formula (I), the stereoisomer thereof or the pharmaceutically acceptable salt thereof, or the pharmaceutical composition thereof for use in preventing or treating a BTK-related disease.

SUMMARY

The present application relates to a compound of formula (I) or a pharmaceutically acceptable salt thereof,

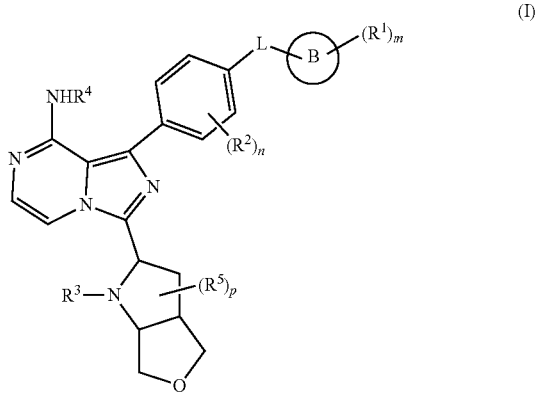

wherein, ring B is selected from the group consisting of 5-10 membered heteroaryl and $C_{6-10}$ aryl;

$R^1$ is independently selected from the group consisting of halogen, —OH, —$NH_2$, cyano, $C_{1-6}$ alkyl and $C_{1-6}$ alkoxy, wherein the $C_{1-6}$ alkyl or $C_{1-6}$ alkoxy is optionally substituted with halogen;

m is 0, 1, 2, 3 or 4;

L is selected from the group consisting of —C(O)NH—, —NHC(O)—, —O—, —NH—, —S—, —C(O)O—, —OC(O)—, —S(O)$_2$O— and —OS(O)$_2$—;

$R^2$ is independently selected from the group consisting of halogen, —OH, —$NH_2$, cyano, $C_{1-6}$ alkyl and $C_{1-6}$ alkoxy, wherein the $C_{1-6}$ alkyl or $C_{1-6}$ alkoxy is optionally substituted with halogen;

n is 0, 1, 2, 3 or 4;

$R^3$ is selected from the group consisting of H, $R^aC(O)$—, $R^aS(O)_2$— and $R^a$—;

$R^5$ is independently selected from the group consisting of halogen, —OH, —$NH_2$, cyano, $C_{1-6}$ alkyl and $C_{1-6}$ alkoxy;

p is 0, 1, 2 or 3;

$R^4$ is selected from the group consisting of hydrogen, $R^aS(O)_2$—, $(R^aO)_2P(O)$— and $R^aC(O)$—;

wherein $R^a$ is independently selected from the group consisting of $C_{2-6}$ alkynyl, $C_{2-6}$ alkenyl, $C_{1-6}$ alkyl, $C_{3-6}$ cycloalkyl, ($C_{1-6}$ alkyl)NH—, ($C_{1-6}$ alkyl)$_2$N—, 3-6 membered heterocycloalkyl, 5-10 membered heteroaryl and $C_{6-10}$ aryl, wherein the $R^a$ is optionally substituted with ($C_{1-6}$ alkyl)$_2$N—, ($C_{1-6}$ alkyl)NH—, hydroxy, amino, halogen or cyano.

In some embodiments, ring B is selected from the group consisting of 5-6 membered heteroaryl and phenyl; in some embodiments, ring B is selected from 6 membered heteroaryl; in some embodiments, ring B is pyridinyl (e.g., pyridin-2-yl).

In some embodiments, $R^1$ is independently selected from the group consisting of halogen, $C_{1-3}$ alkyl and $C_{1-3}$ alkoxy, wherein the $C_{1-3}$ alkyl or $C_{1-3}$ alkoxy is optionally substituted with halogen; in some embodiments, $R^1$ is independently selected from the group consisting of halogen and $C_{1-3}$ alkyl optionally substituted with fluorine; in some embodiments, $R^1$ is trifluoromethyl.

In some embodiments, m is 0, 1 or 2; in some embodiments, m is 0 or 1.

In some embodiments, ring B is pyridin-2-yl, m is 1, and $R^1$ is trifluoromethyl; in some embodiments, $R^1$ is at the 4-position of the pyridine ring.

In some embodiments, ring B is pyridin-2-yl, and m is 0.

In some embodiments, L is selected from the group consisting of —C(O)NH—, —NHC(O)—, —C(O)O— and —OC(O)—; in some embodiments, L is —C(O)NH—.

In some embodiments, $R^2$ is independently selected from the group consisting of halogen, —OH, —$NH_2$, $C_{1-3}$ alkyl and $C_{1-3}$ alkoxy; in some embodiments, $R^2$ is independently selected from halogen; in some embodiments, $R^2$ is independently fluorine.

In some embodiments, n is 0, 1 or 2; in some embodiments, n is 0 or 1.

In some embodiments, n is 1 and $R^2$ is fluorine. In some embodiments, n is 0.

In some embodiments, $R^3$ is selected from the group consisting of H, $R^aC(O)$— and $R^aS(O)_2$—.

In some embodiments, $R^a$ is independently selected from the group consisting of $C_{2-6}$ alkynyl, $C_{2-6}$ alkenyl, $C_{1-6}$ alkyl, $C_{3-6}$ cycloalkyl, ($C_{1-6}$ alkyl)NH—, ($C_{1-6}$ alkyl)$_2$N—, 3-6 membered heterocycloalkyl, 5-10 membered heteroaryl and $C_{6-10}$ aryl, wherein the $R^a$ is optionally substituted with ($C_{1-3}$ alkyl)$_2$N—, ($C_{1-3}$ alkyl)NH—, hydroxy or amino; in some embodiments, $R^a$ is independently selected from the group consisting of $C_{2-3}$ alkynyl, $C_{2-3}$ alkenyl, $C_{1-3}$ alkyl, $C_{3-4}$ cycloalkyl, ($C_{1-3}$ alkyl)NH— and ($C_{1-3}$ alkyl)$_2$N—, wherein the $R^a$ is optionally substituted with ($C_{1-3}$ alkyl)$_2$N—, ($C_{1-3}$ alkyl)NH—, hydroxy or amino; in some embodiments, $R^a$ is independently selected from the group consisting of propynyl, $C_{2-3}$ alkenyl, methyl, cyclopropyl, cyclobutyl, $CH_3NH$—, $(CH_3)_2CHNH$— and $(CH_3)_2N$—, wherein the methyl, $C_{2-3}$ alkenyl and cyclopropyl are optionally substituted with $(CH_3)_2N$—, hydroxy or amino.

In some embodiments, $R^3$ is selected from the group consisting of H, $CH_3C≡CC(O)$—, $(CH_3)_2NCH_2CH=CHC(O)$—, $CH_2=CHC(O)$—, $CH_3C(O)$—, $(CH_3)_2CHNHS(O)_2$—, $HOCH_2C(O)$—, $H_2NCH_2C(O)$—, cyclobutyl-C(O)—, $(CH_3)_2NS(O)_2$—, $CH_3NHS(O)_2$— and cyclopropyl-C(O)— optionally substituted with hydroxy. In some embodiments, $R^3$ is selected from the group consisting of $CH_3C≡CC(O)$—, $CH_2=CHC(O)$— and cyclopropyl-C(O)—. In some embodiments, $R^3$ is selected from $CH_3C≡CC(O)$—.

In some embodiments, $R^3$ is selected from $R^aC(O)$—, wherein $R^a$ is selected from the group consisting of $C_{2-6}$ alkynyl, $C_{2-6}$ alkenyl, $C_{1-6}$ alkyl, $C_{3-6}$ cycloalkyl, ($C_{1-6}$ alkyl)NH—, ($C_{1-6}$ alkyl)$_2$N—, 3-6 membered heterocycloalkyl, 5-10 membered heteroaryl and $C_{6-10}$ aryl, wherein the $R^a$ is optionally substituted with ($C_{1-3}$ alkyl)$_2$N—, ($C_{1-3}$ alkyl)NH—, hydroxy or amino; in some embodiments, $R^a$ is selected from the group consisting of $C_{2-3}$ alkynyl, $C_{2-3}$ alkenyl, $C_{1-3}$ alkyl, $C_{3-4}$ cycloalkyl, ($C_{1-3}$ alkyl)NH— and ($C_{1-3}$ alkyl)$_2$N—, wherein the $R^a$ is optionally substituted with ($C_{1-3}$ alkyl)$_2$N—, ($C_{1-3}$ alkyl)NH—, hydroxy or amino; in some embodiments, $R^a$ is selected from the group consisting of propynyl, $C_{2-3}$ alkenyl, methyl, cyclopropyl, cyclobutyl, $CH_3NH$—, $(CH_3)_2CHNH$— and $(CH_3)_2N$—, wherein the methyl, $C_{2-3}$ alkenyl and cyclopropyl are optionally substituted with $(CH_3)_2N$—, hydroxy or amino; in some embodiments, $R^a$ is selected from the group consisting of $CH_3C≡C$—, $(CH_3)_2NCH_2CH=CH$—, $CH_2=CH$—, $CH_3$—, $HOCH_2$—, $H_2NCH_2$—, cyclobutyl, cyclopropyl and

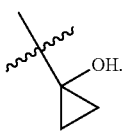

In some embodiments, $R^3$ is selected from $R^aS(O)_2$—, wherein $R^a$ is selected from the group consisting of $C_{2-6}$ alkynyl, $C_{2-6}$ alkenyl, $C_{1-6}$ alkyl, $C_{3-6}$ cycloalkyl, $(C_{1-6}$ alkyl)NH—, $(C_{1-6}$ alkyl)$_2$N—, 3-6 membered heterocycloalkyl, 5-10 membered heteroaryl and $C_{6-10}$ aryl, wherein the $R^a$ is optionally substituted with $(C_{1-3}$ alkyl)$_2$N—, $(C_{1-3}$ alkyl)NH—, hydroxyl or amino; in some embodiments, $R^a$ is selected from the group consisting of $C_{2-3}$ alkynyl, $C_{2-3}$ alkenyl, $C_{1-3}$ alkyl, $C_{3-4}$ cycloalkyl, $(C_{1-3}$ alkyl)NH— and $(C_{1-3}$ alkyl)$_2$N—, wherein the $R^a$ is optionally substituted with $(C_{1-3}$ alkyl)$_2$N—, $(C_{1-3}$ alkyl)NH—, hydroxy or amino; in some embodiments, $R^a$ is selected from the group consisting of propynyl, $C_{2-3}$ alkenyl, methyl, cyclopropyl, cyclobutyl, $CH_3NH$—, $(CH_3)_2CHNH$— and $(CH_3)_2N$—, wherein the methyl, $C_{2-3}$ alkenyl and cyclopropyl are optionally substituted with $(CH_3)_2N$—, hydroxy or amino; in some embodiments, $R^a$ is selected from the group consisting of $(CH_3)_2CHNH$—, $(CH_3)_2N$- and $CH_3NH$—.

In some embodiments, $R^5$ is independently selected from the group consisting of —F, —OH, —$NH_2$, methyl and methoxy.

In some embodiments, p is 0, 1 or 2; in some embodiments, p is 0.

In some embodiments, $R^4$ is selected from the group consisting of hydrogen, $R^aS(O)_2$— and $(R^aO)_2P(O)$—; in some embodiments, $R^4$ is selected from the group consisting of hydrogen, $C_{3-6}$ cycloalkyl-S(O)$_2$— and $(C_{1-6}$ alkyl-O)$_2$P(O)—; in some embodiments, $R^4$ is selected from the group consisting of hydrogen, cyclopropyl-S(O)$_2$and $(CH_3O)_2$—P(O)—; in some embodiments, $R^4$ is hydrogen.

In some embodiments, the compound of formula (I), the stereoisomer thereof or the pharmaceutically acceptable salt thereof disclosed herein is a compound of formula (II), a stereoisomer thereof or a pharmaceutically acceptable salt thereof,

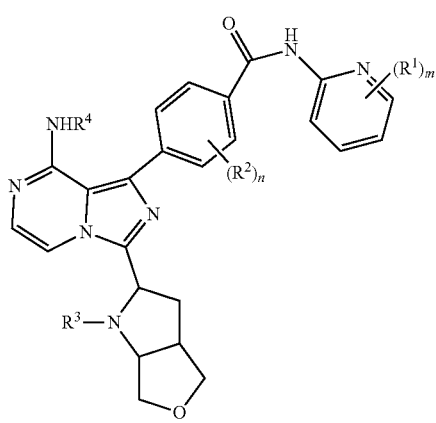

(II)

wherein $R^1$, $R^2$, $R^3$, $R^4$, m and n are defined as above.

In some embodiments, the compound of formula (I), the stereoisomer thereof or the pharmaceutically acceptable salt thereof disclosed herein is a compound of formula (III), a stereoisomer thereof or a pharmaceutically acceptable salt thereof,

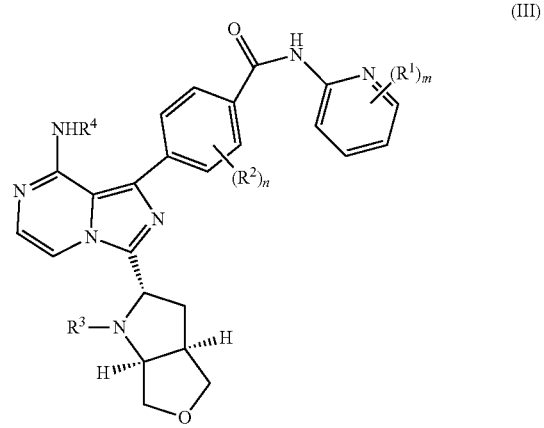

(III)

wherein $R^1$, $R^2$, $R^3$, $R^4$, m and n are defined as above.

In some embodiments, the compound of formula (I), the stereoisomer thereof or the pharmaceutically acceptable salt thereof disclosed herein is a compound of formula (IV), a stereoisomer thereof or a pharmaceutically acceptable salt thereof,

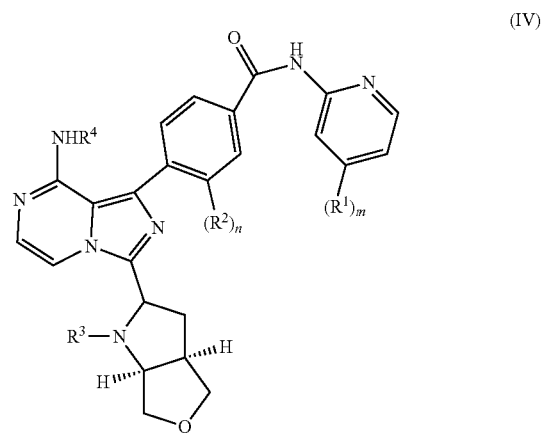

(IV)

wherein $R^1$, $R^2$, $R^3$ and $R^4$ are defined as above, m is 0 or 1, and n 0 or 1. When n is 0, $R^2$ is absent, i.e., the phenyl ring is unsubstituted. When m is 0, $R^1$ is absent, i.e., the pyridine ring is unsubstituted.

In some embodiments, the compound of formula (I), the stereoisomer thereof or the pharmaceutically acceptable salt thereof is selected from the compound of the following structural formulas, a stereoisomer thereof or a pharmaceutically acceptable salt thereof:

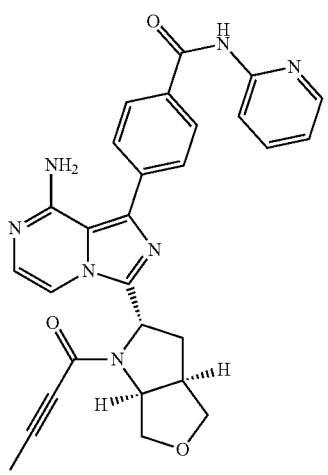
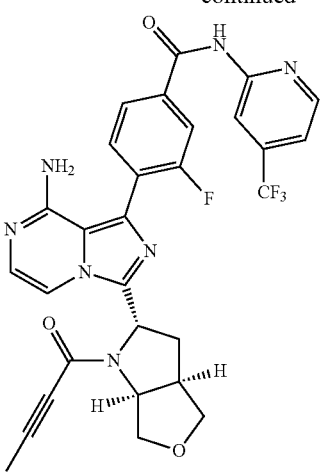
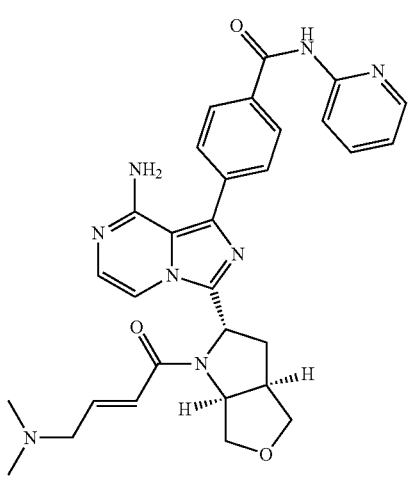
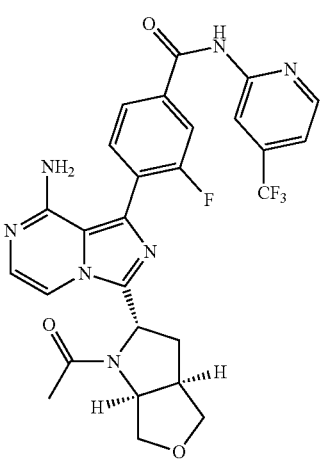
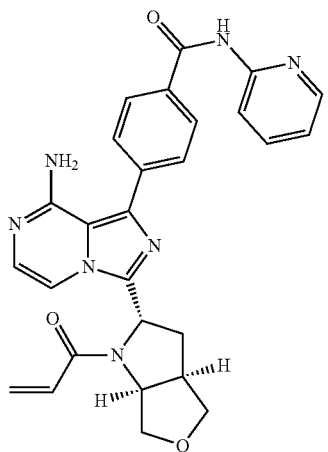
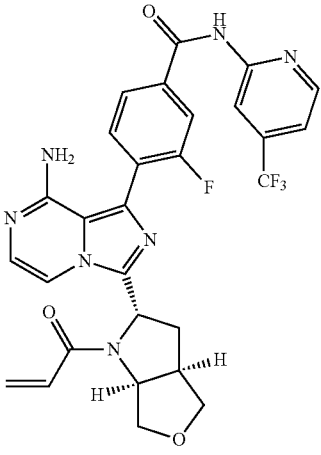

9
-continued
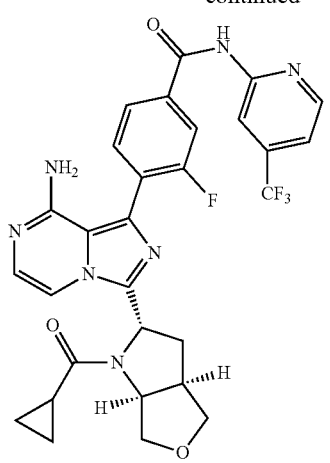
10
-continued
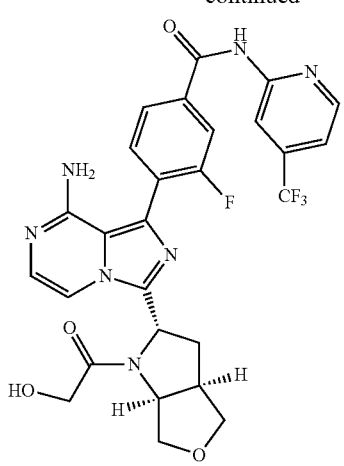
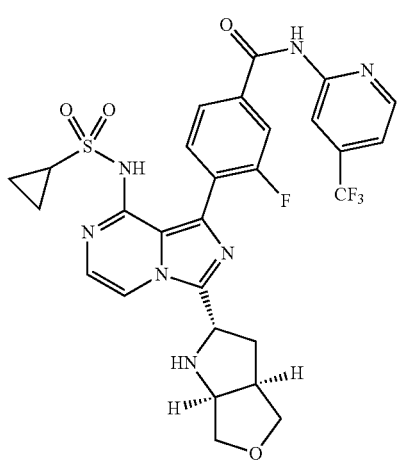
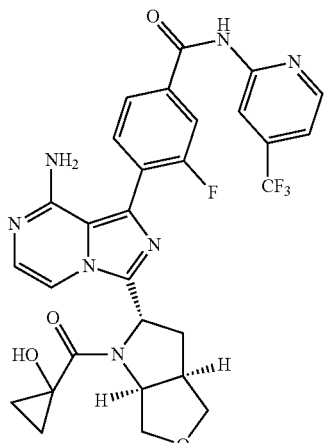
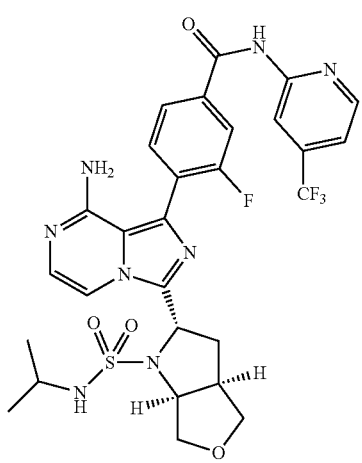
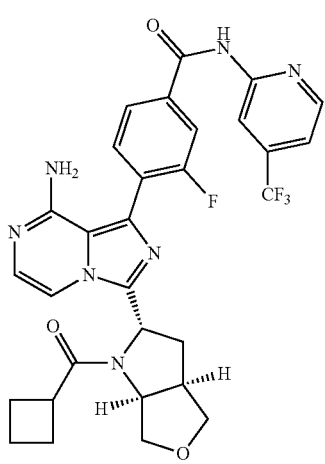

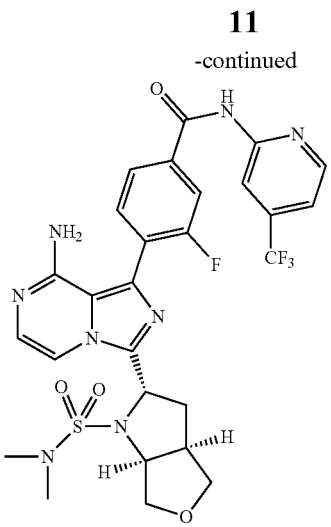
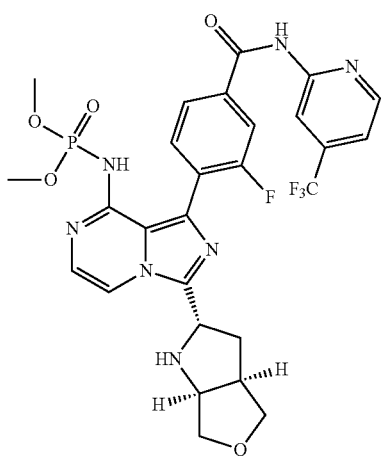
and
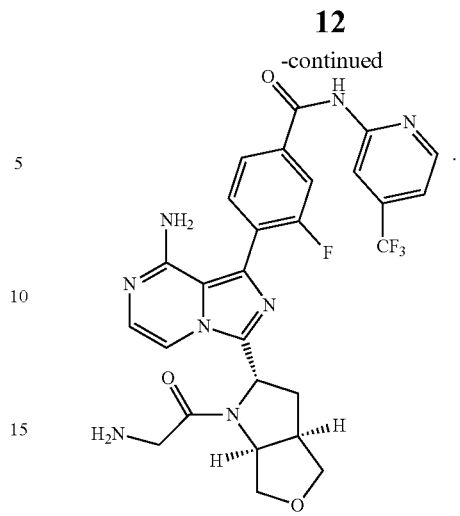

In another aspect, the present application relates to a pharmaceutical composition comprising the compound of formula (I), the stereoisomer thereof or the pharmaceutically acceptable salt thereof. In some embodiments, the pharmaceutical composition disclosed herein further comprises a pharmaceutically acceptable excipient.

In another aspect, the present application relates to a method for preventing or treating a BTK-related disease in a mammal, comprising administering to a mammal, preferably a human, in need of the treatment a therapeutically effective amount of the compound of formula (I), the stereoisomer thereof or the pharmaceutically acceptable salt thereof, or the pharmaceutical composition thereof.

In another aspect, the present application relates to use of the compound of formula (I), the stereoisomer thereof or the pharmaceutically acceptable salt thereof, or the pharmaceutical composition thereof in preparing a medicament for preventing or treating a BTK-related disease.

In another aspect, the present application relates to use of the compound of formula (I), the stereoisomer thereof or the pharmaceutically acceptable salt thereof, or the pharmaceutical composition thereof in preventing or treating a BTK-related disease.

In another aspect, the present application relates to the compound of formula (I), the stereoisomer thereof or the pharmaceutically acceptable salt thereof, or the pharmaceutical composition thereof for use in preventing or treating a BTK-related disease.

In some embodiments, the BTK-related disease is a BTK-mediated disease. In some embodiments, the BTK-related disease is selected from autoimmune diseases, inflammatory diseases and cancer. In some embodiments, the BTK-related disease is diffuse large B-cell lymphoma.

Definitions

Unless otherwise stated, the following terms used in the present application shall have the following meanings. A specific term, unless otherwise specifically defined, should not be considered uncertain or unclear, but construed according to its common meaning in the field. When referring to a trade name, it is intended to refer to its corresponding commercial product or its active ingredient.

The term "substituted" means that any one or more hydrogen atoms on a specific group are substituted by substituents, as long as the valence of the specific group is normal and the resulting compound is stable. When the substituent is oxo (namely =O), it means that two hydrogen atoms are substituted, and oxo is not available on an aromatic group.

The terms "optional" or "optionally" means that the subsequently described event or circumstance may, but not necessarily, occur. The description includes instances where the event or circumstance occurs and instances where the event or circumstance does not occurs. For example, an ethyl optionally substituted by halogen, means that the ethyl may be unsubstituted (CH$_2$CH$_3$), monosubstituted (for example, CH$_2$CH$_2$F), polysubstituted (for example, CHFCH$_2$F, CH$_2$CHF$_2$ and the like) or fully substituted (CF$_2$CF$_3$). It will be understood by those skilled in the art that for any group comprising one or more substituents, any substitution or substituting pattern which may not exist or cannot be synthesized spatially is not introduced.

C$_{m-n}$ used herein means that the portion has an integer number of carbon atoms in the given range. For example, "C$_{1-6}$" means that the group may have 1 carbon atom, 2 carbon atoms, 3 carbon atoms, 4 carbon atoms, 5 carbon atoms or 6 carbon atoms.

When any variable (e.g., R) occurs more than once in the constitution or structure of a compound, the definition of the variable in each case is independent. For example, if a group contains 2R, the definition of each R is independent.

For

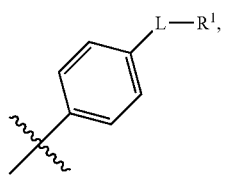

when L is —CO(NH)—, it means that

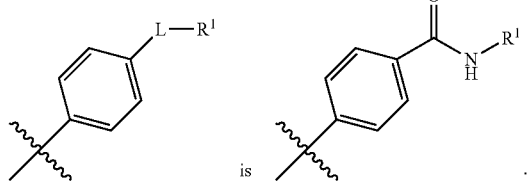

For

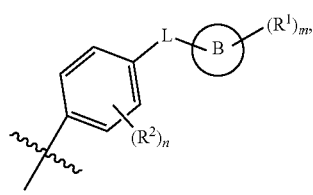

when L is —CO(NH)—, it means that

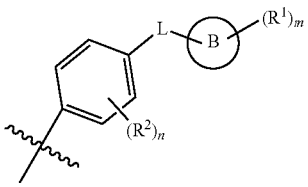

is

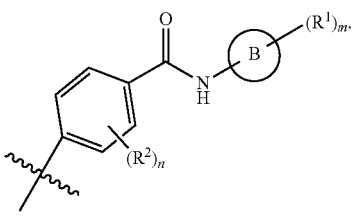

The term "halo-" or "halogen" refers to fluorine, chlorine, bromine and iodine.

The term "hydroxy" refers to —OH group.

The term "amino" refers to —NH$_2$ group.

The term "cyano" refers to —CN group.

The term "alkyl" refers to hydrocarbyl with a general formula C$_n$H$_{2n+1}$, for example, C$_{1-6}$ alkyl and C$_{1-3}$ alkyl. The alkyl can be linear or branched. For example, the term "C$_{1-6}$ alkyl" refers to alkyl with 1-6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). The alkyl moiety (namely alkyl) of alkoxy, alkylamino, dialkylamino, alkylsulfonyl and alkylthio is similarly defined as above.

The term "alkoxy" refers to —O-alkyl, for example, —O—C$_{1-6}$ alkyl and —O—C$_{1-3}$ alkyl.

The term "alkenyl" refers to linear or branched unsaturated aliphatic hydrocarbyl consisting of carbon atoms and hydrogen atoms with at least one double bond, for example, C$_{2-6}$ alkenyl and C$_{2-3}$ alkenyl. Non-limiting examples of alkenyl include, but are not limited to, ethenyl, 1-propenyl, 2-propenyl, 1-butenyl, isobutenyl, 1,3-butadienyl, and the like.

The term "alkynyl" refers to linear or branched unsaturated aliphatic hydrocarbyl consisting of carbon atoms and hydrogen atoms with at least one triple bond, for example, C$_{2-6}$ alkynyl and C$_{2-3}$ alkynyl. Non-limiting examples of alkynyl include, but are not limited to, ethynyl (—C≡CH), 1-propinyl (—C≡C—CH$_3$), 2-propinyl (—CH$_2$—C≡CH), 1,3-butadiynyl (—C≡C—C≡CH), and the like.

The term "cycloalkyl" refers to a carbon ring that is fully saturated and may exist as a monocyclic, bridged cyclic or spiro structure. Unless otherwise specified, the carbon ring is generally a 3-10 membered ring or 3-6 membered ring. Non-limiting examples of cycloalkyl include, but are not limited to, cyclopropyl, cyclobutyl, cyclopentyl, cyclohexyl, norbornyl (bicyclo[2.2.1]heptyl), bicyclo[2.2.2]octyl, adamantyl, and the like.

The term "heterocycloalkyl" refers to a cyclic group that is fully saturated and may exist as a monocyclic, fused polycyclic, bridged cyclic or spiro structure. Unless otherwise specified, the heterocyclyl is generally a 3-7 membered ring containing 1-3 heteroatoms (preferably 1 or 2 heteroatoms) independently selected from the group consisting of sulfur, oxygen and/or nitrogen, or is generally a 3-6 membered ring containing 1-3 heteroatoms (preferably 1 or 2 heteroatoms) independently selected from the group consisting of sulfur, oxygen and/or nitrogen. The heterocycloalkyl may be a 3-6 membered ring containing 1 or 2 heteroatoms independently selected from the group consisting of oxygen and nitrogen. Examples of 3 membered heterocycloalkyl include, but are not limited to, oxiranyl, thietanyl, and aziranyl. Non-limiting examples of 4 membered heterocycloalkyl include, but are not limited to, azetidinyl, oxetanyl, and thietanyl. Examples of 5 membered heterocycloalkyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl, and tetrahydropyrazolyl. Examples of 6 membered heterocycloalkyl include, but are not limited to, piperidinyl, tetrahydropyranyl, tetrahydrothiopyranyl, morpholinyl, piperazinyl, 1,4-oxathianyl, 1,4-dioxanyl, sulfomorpholinyl, 1,3-dithianyl, and 1,4-dithianyl. Examples of 7 membered heterocycloalkyl include, but are not limited to, azacycloheptanyl, oxacycloheptanyl, and thiocycloheptanyl. Preferably, the heterocycloalkyl is a monocyclic heterocycloalkyl with 5 or 6 ring atoms.

The term "aryl" refers to an aromatic monocyclic or fused polycyclic group of carbon atoms with the conjugated pi-electron system. For example, an aryl may have 6-20 carbon atoms, 6-14 carbon atoms, 6-12 carbon atoms, or 6-10 carbon atoms. Non-limiting examples of aryl includes, but are not limited to, phenyl, naphthyl, anthryl, 1,2,3,4-tetrahydronaphthalenyl, and the like.

The term "heteroaryl" refers to a monocyclic or fused polycyclic system which comprises at least one ring atom selected from the group consisting of N, O and S, with the remaining ring atoms being C, and which has at least one aromatic ring. Preferably, the heteroaryl has a single 4-8 membered ring, in particular, a 5-8 membered ring, or is a plurality of fused rings comprising 6-14 ring atoms, in particular 6-10 ring atoms. Non-limiting examples of heteroaryl include, but are not limited to, pyrrolyl, furanyl, thienyl, imidazolyl, oxazolyl, pyrazolyl, pyridinyl, pyrimidinyl, pyrazinyl, quinolyl, isoquinolyl, tetrazolyl, triazolyl, triazinyl, benzofuranyl, benzothienyl, indolyl, isoindolyl and the like.

The term "treating" means administering the compound or formulation described herein to ameliorate or eliminate a disease or one or more symptoms related to the disease, and includes:

(i) inhibiting a disease or disease state, i.e., arresting its development;

(ii) alleviating a disease or disease state, i.e., causing its regression.

The term "preventing" means administering the compound or formulation described herein to prevent a disease or one or more symptoms related to the disease, and includes: preventing the occurrence of the disease or disease state in a mammal, particularly when such a mammal is predisposed to the disease state but has not yet been diagnosed as having it.

The term "therapeutically effective amount" refers to an amount of the compound disclosed herein for (i) treating or preventing a specific disease, condition or disorder; (ii) alleviating, improving or eliminating one or more symptoms of a specific disease, condition or disorder, or (iii) preventing or delaying onset of one or more symptoms of a specific disease, condition or disorder described herein. The amount of the compound disclosed herein composing the "therapeutically effective amount" varies dependently on the compound, the disease state and its severity, the administration regimen, and the age of the mammal to be treated, but can be determined routinely by those skilled in the art in accordance with their knowledge and the present disclosure.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

A pharmaceutically acceptable salt, for example, may be a metal salt, an ammonium salt, a salt formed with an organic base, a salt formed with an inorganic acid, a salt formed with an organic acid, a salt formed with a basic or acidic amino acid, and the like.

The term "pharmaceutical composition" refers to a mixture consisting of one or more of the compounds or pharmaceutically acceptable salts thereof disclosed herein and a pharmaceutically acceptable excipient. The pharmaceutical composition is intended to facilitate the administration of the compound to an organic entity.

The term "pharmaceutically acceptable excipients" refers to those which do not have a significant irritating effect on an organic entity and do not impair the biological activity and properties of the active compound. Suitable excipients are well known to those skilled in the art, such as carbohydrate, wax, water-soluble and/or water-swellable polymers, hydrophilic or hydrophobic material, gelatin, oil, solvent, water.

The word "comprise" and variations thereof such as "comprises" or "comprising" will be understood in an open, non-exclusive sense, i.e., "including but not limited to".

The compounds and intermediates disclosed herein may also exist in different tautomeric forms, and all such forms are included within the scope of the present application. The term "tautomer" or "tautomeric form" refers to structural isomers of different energies that can interconvert via a low energy barrier. For example, a proton tautomer (also referred to as prototropic tautomer) includes interconversion via proton transfer, such as keto-enol isomerization and imine-enamine isomerization. A specific example of a proton tautomer is an imidazole moiety where a proton can transfer between two ring nitrogens. A valence tautomer includes the interconversion via recombination of some bonding electrons.

The present application also comprises isotopically-labeled compounds which are identical to those recited herein but one or more atoms thereof are replaced by an atom having an atomic mass or mass number different from the atomic mass or mass number usually found in nature. Examples of isotopes that can be incorporated into the compounds disclosed herein include isotopes of hydrogen, carbon, nitrogen, oxygen, phosphorus, sulfur, fluorine, iodine, and chlorine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$.

Certain isotopically-labeled compounds disclosed herein (e.g., those labeled with $^3H$ and $^{14}C$) can be used to analyze compounds and/or substrate tissue distribution. Tritiated (i.e., $^3H$) and carbon-14 (i.e., $^{14}C$) isotopes are particularly preferred for their ease of preparation and detectability. Positron emitting isotopes, such as $^{15}O$, $^{13}N$, $^{11}C$, and $^{18}F$ can be used in positron emission tomography (PET) studies to determine substrate occupancy. Isotopically-labeled compounds disclosed herein can generally be prepared by following procedures analogous to those disclosed in the schemes and/or examples below while substituting a non-isotopically labeled reagent with an isotopically-labeled reagent.

Furthermore, substitution with heavier isotopes such as deuterium (i.e., $^2$H) may provide certain therapeutic advantages (e.g., increased in vivo half-life or reduced dosage requirement) resulting from greater metabolic stability and hence may be preferred in some circumstances in which deuterium substitution may be partial or complete, wherein partial deuterium substitution refers to substitution of at least one hydrogen with at least one deuterium.

The compound disclosed herein can be asymmetrical, for example, has one or more stereoisomers. Unless otherwise stated, all stereoisomers are included, for example, enantiomers and diastereoisomers. The compound with asymmetrical carbon atoms disclosed herein can be separated in an optically pure form or in a racemic form. The optically pure form can be separated from a racemic mixture or can be synthesized using a chiral raw material or a chiral reagent.

The pharmaceutical composition disclosed herein can be prepared by combining the compound disclosed herein with a suitable pharmaceutically acceptable excipient, and can be formulated, for example, into a solid, semisolid, liquid, or gaseous formulation such as tablet, pill, capsule, powder, granule, ointment, emulsion, suspension, suppository, injection, inhalant, gel, microsphere, aerosol, and the like.

Typical routes of administration of a compound or a pharmaceutically acceptable salt thereof or a pharmaceutical composition thereof disclosed herein include, but are not limited to, oral, rectal, local, inhalation, parenteral, sublingual, intravaginal, intranasal, intraocular, intraperitoneal, intramuscular, subcutaneous and intravenous administrations.

The pharmaceutical composition disclosed herein can be manufactured by methods well known in the art, such as by conventional mixing, dissolving, granulating, dragee-making, levigating, emulsifying, lyophilizing, and the like.

In some embodiments, the pharmaceutical composition is in an oral form. For oral administration, the pharmaceutical composition can be formulated by mixing the active compounds with pharmaceutically acceptable excipients well known in the art. These excipients enable the compounds disclosed herein to be formulated into tablets, pills, pastilles, dragees, capsules, liquids, gels, slurries, suspensions and the like for oral administration to a patient.

A solid oral composition can be prepared by conventional mixing, filling or tableting. For example, it can be obtained by the following method: mixing the active compounds with solid excipients, optionally grinding the resulting mixture, adding additional suitable excipients if desired, and processing the mixture into granules to get the core parts of tablets or dragees. Suitable excipients include, but are not limited to: binders, diluents, disintegrants, lubricants, glidants, sweeteners or flavoring agents and the like.

The pharmaceutical compositions may also be suitable for parenteral administration, such as sterile solutions, suspensions or lyophilized products in suitable unit dosage forms.

In all of the administration methods of the compound of general formula I described herein, the daily dose administered is from 0.01 mg/kg to 200 mg/kg body weight, given in individual or separated doses.

The compounds disclosed herein can be prepared by a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples disclosed herein.

The chemical reactions of the embodiments disclosed herein are carried out in a suitable solvent that must be suitable for the chemical changes in the present application and the reagents and materials required therefor. In order to acquire the compounds disclosed herein, it is sometimes necessary for one skilled in the art to modify or select a synthesis procedure or a reaction scheme based on the existing embodiments.

An important consideration in synthesis route planning in the art is the selection of suitable protecting groups for reactive functional groups (e.g., amino in the present application). For example, reference may be made to Greene's Protective Groups in Organic Synthesis (4th Ed.) Hoboken, New Jersey: John Wiley & Sons, Inc. All references cited herein are incorporated by reference in their entirety.

In some embodiments, the compound of general formula (I) disclosed herein may be prepared by one skilled in the art of organic synthesis using methods known in the art by the following routes:

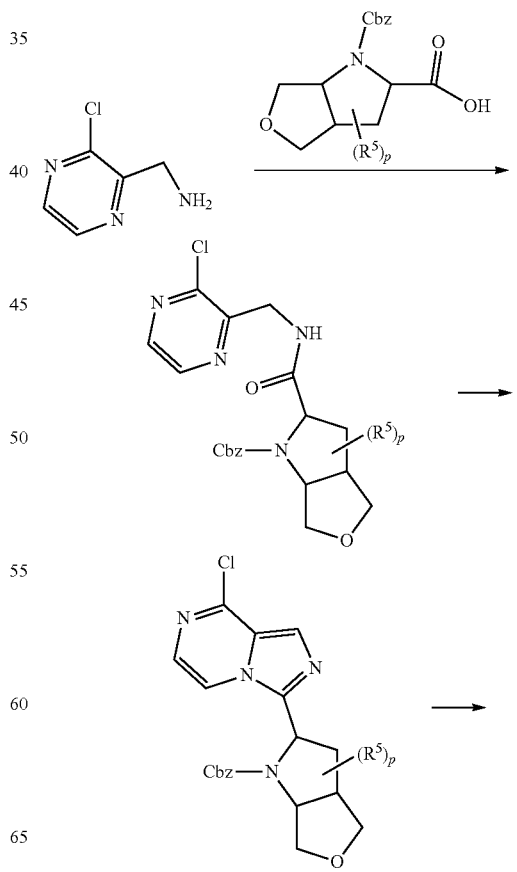

19
-continued

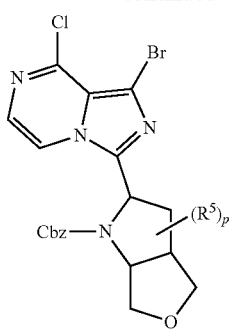 

20
-continued

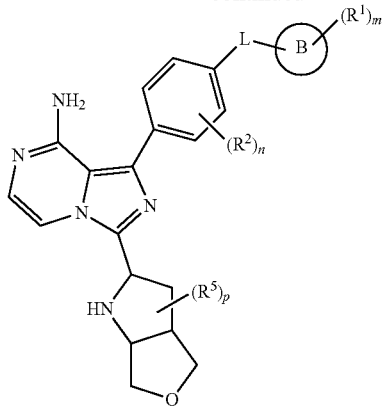

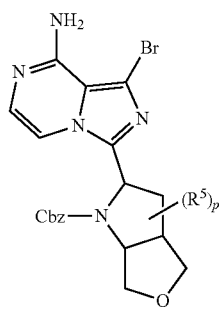 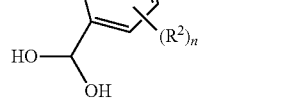

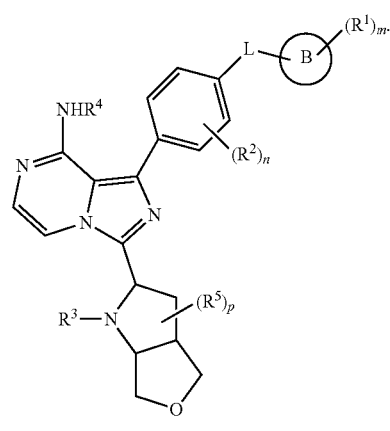

(I)

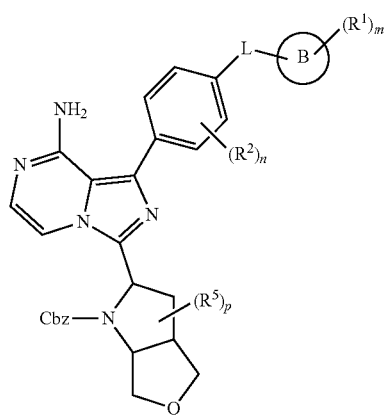 

The following abbreviations are used in this application:

PE represents petroleum ether; EA represents ethyl acetate; DMSO represents dimethyl sulfoxide; DMF represents N,N-dimethylformamide; DCM represents dichloromethane; NBS represents N-bromosuccinimide; DIPEA represents diisopropylethylamine; MeOH represents methanol; EDTA represents ethylenediamine tetraacetic acid; DTT represents dithiothreitol; EGTA represents ethylene glycol-bis-(2-aminoethylether)-N,N,N',N'-tetraacetic acid; HEPES represents 4-hydroxyethylpiperazine ethanesulfonic acid; HATU represents 2-(7-benzotriazole oxide)-N,N,N',N'-tetramethyluronium hexafluorophosphate; TLC represents thin-layer chromatography; MeCN represents acetonitrile; TEA represents triethylamine; T3P represents 1-n-propylphosphoric anhydride; Cbz for benzyloxycarbonyl; Cbz-Cl represents benzyl chloroformate; Py represents pyridine; TFA represents trifluoroacetic acid; THF represents tetrahydrofuran; DMAP represents 4-dimethylaminopyridine.

For clarity, the present application is further described with the following examples, which are, however, not intended to limit the scope of the present application. All reagents used in the present application are commercially available and can be used without further purification.

EXAMPLE 1: PREPARATION OF (2S,3AR,6AS)-1-((BENZYL)CARBONYL)HEXAHYDRO-1H-FURAN[3,4-B]PYRROLE-2-CARBOXYLIC ACID (A)

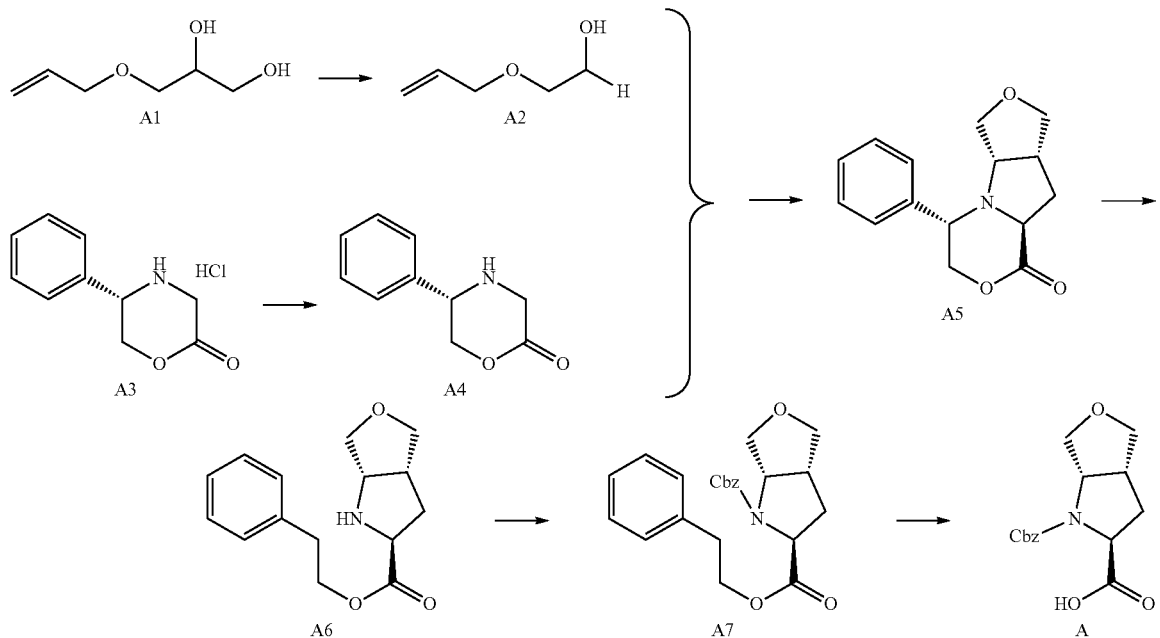

Step 1: Preparation of 2-(allyloxy)acetaldehyde (Intermediate A2)

To a reaction flask were added water (178 mL) at 70° C. and sodium periodate (97 g). 300-400 mesh silica gel (378 g) was added while vigorously stirring. The mixture was stirred for 3 min to give sodium periodate/silica gel oxidant. To a reaction flask were added DCM (1120 mL), and a solution of intermediate A1 (60 g) in DCM (1120 mL) while stirring. The mixture was stirred overnight. After the reaction was completed, the reaction mixture was filtered. The filter cake was rinsed with chloroform (200 mL×3). The filtrates were combined and concentrated to give an oily product, which was distilled under reduced pressure to collect a fraction (40 mbar) at a vapor temperature of 46° C., namely intermediate A2 (30 g).

$^1$H NMR (500 MHz, DMSO-d6): δ 9.59 (s, 1H), 5.94-5.84 (m, 1H), 5.30-5.19 (m, 2H), 4.16 (s, 2H), 4.04-4.03 (d, J=5.0 Hz, 2H)

Step 2: Preparation of (3aS,5S,8aS,9aR)-5-phenyloctahydro-8H-furo[3',4':4,5]pyrrolo[2,1-c][1,4]oxazin-8-one (intermediate A5)

(S)-5-phenylmorpholin-2-one hydrochloride (4 g) was dissolved in water (100 mL). The solution was adjusted to pH 8-9 with saturated sodium bicarbonate and extracted with DCM (50 mL×3). The organic phases were combined, washed twice with saturated sodium chloride solution, and concentrated to give a residue (3.1 g). The residue was transferred to a reaction flask, benzene (20 mL) was added, followed by 2-(allyloxy)acetaldehyde (intermediate A2, 1.77 g). The mixture was dissolved by stirring and added with benzene (20 mL). After being stirred at room temperature for 1 h, the reaction mixture was heated to reflux for 12 h, and concentrated to remove benzene after the heating was stopped. The residue was added with water (100 mL) and extracted with EA (100 mL×3). The organic phases were combined, washed saturated sodium chloride solution (100 mL×2), dried over anhydrous sodium sulfate and filtered, and the filtrate was concentrated to give a residue. The residue was slurried with n-hexane (100 mL×2) and filtered to give intermediate A5 (4.12 g).

$^1$H NMR (500 MHz, DMSO-d6): δ 7.48-7.47 (m, 2H), 7.39-7.36 (m, 2H), 7.32-7.31 (m, 1H), 4.33-4.31 (m, 1H), 4.28-4.26 (m, 2H), 4.01-3.98 (m, 1H), 3.60-3.58 (m, 1H), 3.50-3.47 (m, 1H), 3.44-3.42 (m, 1H), 3.32-3.28 (m, 1H), 3.20-3.17 (m, 1H), 2.79-2.78 (m, 1H), 2.52-2.49 (m, 1H), 1.86-1.84 (m, 1H). MS(ESI, [M+H]$^+$) m/z: 260.3.

Step 3: preparation of (2S,3aR,6aS)-1-((benzyloxy)carbonyl)hexahydro-1H-furo[3,4-b]pyrrole-2-carboxylic acid (intermediate A)

To a reaction flask were added intermediate A5 (15 g), MeOH (1.380 L), TFA (41.1 g) and Pd(OH)$_2$ (6.95 g). The mixture was reacted overnight at room temperature under H$_2$ atmosphere, and filtered to remove palladium hydroxide. The reaction solution was concentrated to give an oily product. The oily product was transferred to a reaction flask, then 1,4-dioxane (414 mL), H$_2$O (276 mL) and sodium bicarbonate (24.31 g) were added. The mixture was cooled to 0° C., added with Cbz-Cl (11.12 g), and reacted overnight after the addition. After the reaction was completed, the reaction solution was concentrated, and the concentrate was extracted with ethyl acetate (300 mL×3). The organic phases were combined and concentrated, and the concentrate was transferred to a reaction flask, then THF (276 mL) and H$_2$O (276 mL) was added. The mixture was dissolved by stirring, added with LiOH (2.60 g), heated to 50° C. and reacted for 2 h before the heating was stopped. The reaction solution was concentrated to remove THF, and extracted with ethyl acetate (300 mL×2). The aqueous phase was retained, adjusted to pH 2-3 with 1 N HCl, and extracted with ethyl acetate (300 mL×2). The organic phases were combined, washed with saturated brine (200 mL×2), dried over anhydrous sodium sulfate, and filtered to remove sodium sulfate, and the filtrate was concentrated to give intermediate A (2.02 g).

$^1$H NMR (500 MHz, DMSO-d$_6$): δ 13.62-11.85 (br, 1H), 7.38-7.30 (m, 5H), 5.14-5.03 (m, 2H), 4.43-4.34 (m, 2H), 3.86-3.79 (m, 1H), 3.64-3.62 (m, 1H), 3.55-3.51 (m, 1H), 3.48-3.45 (m, 1H), 2.96-2.83 (m, 1H), 2.19-2.17 (m, 1H), 2.06-1.98 (m, 1H). HR-MS(ESI, [M–H]$^-$) m/z: 290.1018.

EXAMPLE 2: PREPARATION OF (4-(PYRIDIN-2-YLCARBAMOYL)PHENYL)BORONIC ACID (INTERMEDIATE F)

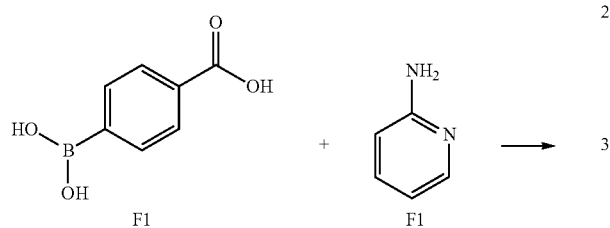

Intermediate F1 (20 g) was added to a reaction flask, and dissolved in DMF (180 mL), then intermediate F2 (13.61 g) and DIPEA (31.2 g) were added at 0° C. The mixture was stirred at 0° C. for 10 min, added with HATU (55 g), and heated to 80° C. and reacted for 5 h under nitrogen atmosphere. After the reaction was completed, the reaction solution was poured into 2-3 fold volume of ice water, stirred uniformly and filtered. The filter cake was washed with ice water and dried to give intermediate F (15.72 g).

$^1$H NMR (500 MHz, DMSO-d6) δ 10.715 (s, 1H), 8.401-8.389 (t, J=6 Hz, 1H), 8.225-8.191 (t, J=17 Hz, 3H), 7.995-7.979 (d, J=8 Hz, 2H), 7.912-7.896 (d, J=8 Hz, 2H), 7.866-7.831 (m, 1H), 7.186-7.160 (m, 1H). MS(ESI, [M+H]+) m/z: 243.3.

EXAMPLE 3: PREPARATION OF (2-FLUORO-4-((4-(TRIFLUOROMETHYL)PYRIDIN-2-YL)CARBAMOYL)PHENYL)BORONIC ACID (INTERMEDIATE G)

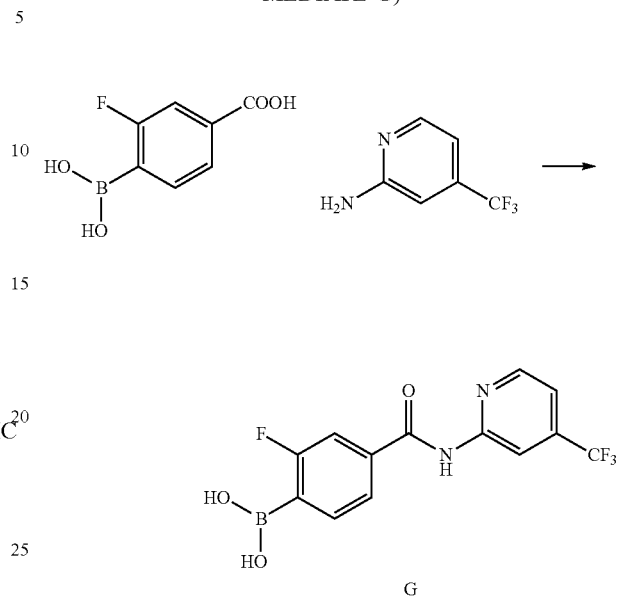

To a reaction flask were added 4-carboxy-2-fluorobenzeneboronic acid (19.4 g), 2-amino-6-(trifluoromethyl)pyridine (17.10 g), DMF (200 mL) and DIPEA (54.5 g) sequentially, then HATU (44.1 g) was added with stirring in an ice-water bath. The mixture was heated to 80° C. and reacted overnight under N$_2$ atmosphere. The reaction solution was cooled to room temperature and added dropwise to ice water being stirred to precipitate a solid, which was then filtered. The filter cake was dried at 50° C. under reduced pressure to give intermediate G (10.71 g).

$^1$H NMR (500 MHz, DMSO-d6): δ11.35 (s, 1H), 8.70-8.69 (d, J=4.5 Hz, 1H), 8.54 (s, 1H), 8.41 (s, 2H), 7.86-7.84 (d, J=8 Hz, 1H), 7.77-7.75 (d, J=9.5 Hz, 1H), 7.70-7.67 (t, J=6.5 Hz, 1H), 7.56-7.55 (d, J=4 Hz, 1H). MS(ESI, [M+H]+) m/z: 329.3.

EXAMPLE 4: PREPARATION OF 4-(8-AMINO-3-((2S,3AR,6AS)-1-(BUT-2-YNOYL)HEXAHYDRO-1H-FURO[3,4-B]PYRROL-2-YL) IMIDAZO[1,5-A]PYRAZIN-1-YL)-N-(PYRIDIN-2-YL)BENZAMIDE (COMPOUND I-1)

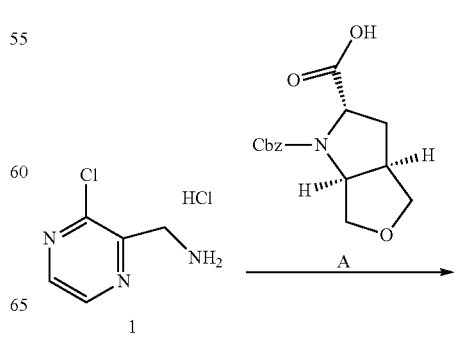

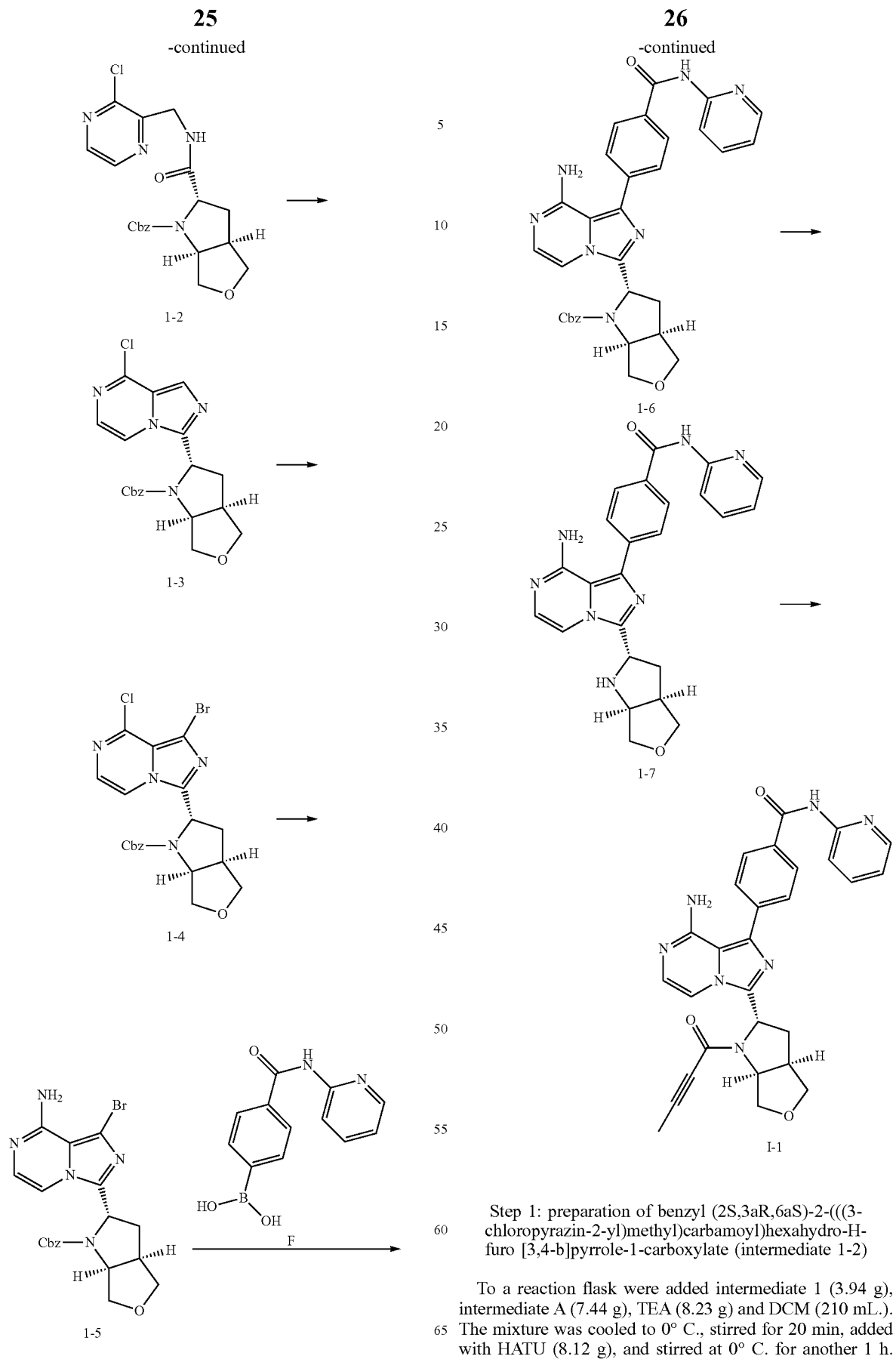
Step 1: preparation of benzyl (2S,3aR,6aS)-2-(((3-chloropyrazin-2-yl)methyl)carbamoyl)hexahydro-H-furo [3,4-b]pyrrole-1-carboxylate (intermediate 1-2)
To a reaction flask were added intermediate 1 (3.94 g), intermediate A (7.44 g), TEA (8.23 g) and DCM (210 mL.). The mixture was cooled to 0° C., stirred for 20 min, added with HATU (8.12 g), and stirred at 0° C. for another 1 h. After the reaction was completed, the reaction solution was washed with 0.1 M HCl solution (200 mL×2), 5% NaHCo₃ solution (200 mL×2), water (200 mL×1) and saturated sodium chloride solution (200 mL×2) sequentially, dried over anhydrous sodium sulfate, and purified by column chromatography to give intermediate 1-2 (6.11 g).

¹H NMR (500 MHz, DMSO-d6): δ 8.62 (br, 1H), 8.51-8.55 (m, 1H), 8.43-8.39 (m, 1H), 7.25-7.39 (m, 5H), 5.13-4.99 (m, 2H), 4.68-4.49 (m, 2H), 4.45-4.41 (m, 2H), 4.86-3.77 (m, 1H), 3.63-3.61 (m, 1H), 3.55-3.45 (m, 2H), 2.95-2.85 (m, 1H), 2.23-2.15 (m, 1H), 2.05-1.92 (m, 1H). MS(ESI, [M+H]+) m/z: 417.3.

Step 2: preparation of benzyl (2S,3aR,6aS)-2-(8-chloroimidazo[1,5-a]pyridin-3-yl)hexahydro-1H-furo[3,4-b]pyrrole-1-carboxylate (intermediate 1-3)

To a reaction flask were added intermediate 1-2 (5 g), MeCN (25 mL) and DMF (25 mL) sequentially, then POCl₃ (6.41 g) was added dropwise in an ice-water bath. After the reaction was completed, the reaction solution was poured into a mixture of ammonium hydroxide (25%, 250 mL) and ice water (500 g). The resulting reaction mixture was stirred, and extracted with ethyl acetate (300 mL×3). The organic phases were combined, washed with saturated brine (200 mL), dried over anhydrous sodium sulfate, filtered and concentrated to give intermediate 1-3 (5.5 g). MS(ESI, [M+H]+) m/z: 399.3.

Step 3: preparation of benzyl (2S,3aR,6aS)-2-(1-bromo-8-chloroimidazo[1,5-a]pyridin-3-yl)hexahydro-1H-furo [3,4-b]pyrrole-1-carboxylate (intermediate 1-4)

To a reaction flask were added intermediate 1-3 (5.05 g) and DMF (70 mL), and the mixture was stirred until all were dissolved. The resulting solution was added with NBS (2.06 g), and reacted at room temperature. After the reaction was completed, the reaction solution was poured into a mixed solution of water (70 mL) and crushed ice (70 g). The resulting reaction mixture was extracted with ethyl acetate (200 mL.×3). The organic phases were combined, washed with saturated brine (200 mL.×2), dried over anhydrous sodium sulfate, filtered and concentrated to give intermediate 1-4 (4.88 g). MS(ESI, [M+H]+) m/z: 477.2.

Step 4: preparation of benzyl (2S,3aR,6a5)-2-(8-amino-1-bromoimidazo[1,5-a]pyridin-3-yl)hexahydro-1H-furo [3,4-b]pyrrole-1-carboxylate (intermediate 1-5)

To a 150 mL sealed tube were added intermediate 1-4 (4.38 g), TEA (1.48 g), and a solution of ammonia in isopropanol (2 M, 108.5 mL) sequentially. The reaction mixture was sealed, and heated to 120° C. and reacted. After the reaction was completed, the reaction solution was concentrated to remove the solvent, and the concentrate was added with crushed ice (100 g). The aqueous phase was adjusted to pH 2-3 with 1 M HCl, and extracted with EA (200 mL×2). The aqueous phase was retained, adjusted to pH 9-10 with 1 M NaOH, and extracted with EA (200 mL×2). The organic phases were combined, washed with water (100 mL×2) and saturated sodium chloride solution (100 mL×2), dried over anhydrous sodium sulfate, and separated by column chromatography to give intermediate 1-5 (2.89 g).

1H NMR (500 MHz, DMSO-d6): δ 7.74-7.60 (m, 1H), 7.37-6.75 (m, 6H), 6.63 (br, 2H), 5.46-5.53 (m, 1H), 5.07-4.72 (m, 2H), 4.55-4.53 (m, 1H), 3.98-3.80 (m, 1H), 3.70-3.54 (m, 3H), 3.21-3.06 (m, 1H), 2.21-2.04 (m, 2H). MS(ESI, [M+H]+) m/z: 458.3

Step 5: preparation of benzyl (2S,3aR,6aS)-2-(8-amino-1-(4-(pyridin-2-ylcarbamoyl)phenyl)imidazo[1,5-a]pyrazin-3-yl)hexahydro-1H-furo[3,4-b]pyrrole-1-carboxylate (intermediate 1-6)

To a sealed tube were added intermediate 1-5 (1.39 g), intermediate F (1.11 g), K₂CO₃ (1.68 g), H₂O (14 mL) and 1,4-dioxane (35.0 mL) sequentially. The mixture was bubbled with N₂ for 10 min, added with [1,1'-bis(diphenylphosphino)ferrocene]palladium(II) dichloride dichloromethane complex (0.62 g), and bubbled with N₂ for 1 min. The reaction mixture was placed in a microwave reactor (at 50 W), and heated to 80° C. and reacted for 20 min. After the reaction was completed, the reaction solution was added with water (20 mL) and extracted with EA (50 mL×3). The combined organic phases were washed with saturated sodium chloride solution (100 mL×2), dried over anhydrous sodium sulfate, filtered and concentrated, and the concentrate was separated by column chromatography to give intermediate 1-6 (1.56 g). MS (ESI, [M+H]+) m/z: 576.4.

Step 6: preparation of 4-(8-amino-3-((2S,3aR,6aS)-hexahydro-1H-furo[3,4-b]pyrrol-2-yl)imidazo[1,5-a]pyrazin-1-yl)-N-(pyridin-2-yl)benzamide (1-7)

A solution of hydrobromic acid (189 mmol) in acetic acid (31.1 mL) was added to intermediate 1-6 (1.46 g) at room temperature, and the mixture was stirred at room temperature for 1 h. After the reaction was completed, the reaction solution was poured into water (50 mL) and extracted with DCM (50 mL×1). The aqueous phase was retained, adjusted to pH 11-14 with 2 M sodium hydroxide solution, and extracted with DCM (50 mL×3). The organic phases were combined, washed with saturated sodium chloride solution (50 mL×2), dried over anhydrous sodium sulfate, filtered and concentrated to give intermediate 1-7 (900 mg).

¹H NMR (500 MHz, DMSO-d6): δ 10.80 (s, 1H), 8.41-8.40 (m, 1H), 8.23-8.21 (m, 1H), 8.17-8.16 (m, 2H), 7.88-7.84 (m, 1H), 7.81-7.80 (m, 1H), 7.77-7.75 (m, 2H), 7.19-7.17 (m, 1H), 7.12-7.11 (m, 1H), 6.14 (br, 2H), 4.74-4.68 (m, 1H), 4.09-4.03 (m, 1H), 3.77-3.74 (m, 1H), 3.70-3.67 (m, 2H), 2.98-2.97 (m, 1H), 2.36-2.33 (m, 1H), 2.05-1.99 (m, 2H). MS(ESI, [M+H]+) m/z: 442.4.

Step 7: preparation of 4-(8-amino-3-((2S,3aR,6aS)-1-(but-2-ynoyl)hexahydro-1H-furo[3,4-b]pyrrol-2-yl)imidazo [1,5-a]pyrazin-1-yl)-N-(pyridin-2-yl)benzamide (compound I-1)

HATU (130 mg) was added to a stirred solution of intermediate 1-7, but-2-ynoic acid (28.8 mg) and triethylamine (0.18 mL) in DCM (20 mL) at room temperature, and the mixture was stirred at room temperature for 30 min. After the reaction was completed, the reaction solution was added with water (20 mL) and DCM (20 mL). The aqueous phase was retained, and concentrated to remove the solvent, and the concentrate was purified by column chromatography to give compound I-1 (50 mg).

¹H NMR (500 MHz, DMSO-d6): δ 10.81 (br, 1H), 8.41-8.40 (m, 1H), 8.23-8.22 (m, 1H), 8.18-8.15 (m, 2H), 7.89-7.84 (m, 1.5H), 7.79-7.73 (m, 2.5H), 7.19-7.16 (m, 1.5H), 7.13-7.12 (m, 0.5H), 6.25-6.08 (br, 2H), 5.91-5.85 (m, 0.5H), 5.69-5.65 (m, 0.5H), 4.85-4.80 (m, 0.5H), 4.70-

4.64 (m, 0.5H), 4.04-3.99 (m, 0.5H), 3.89-3.83 (m, 1H), 3.75-3.58 (m, 2.5H), 3.41-3.35 (m, 0.5H), 3.24-3.18 (m, 0.5H), 2.29-2.17 (m, 1.5H), 2.19-2.11 (m, 0.5H), 2.05-1.99 (m, 1.5H), 1.70-1.64 (m, 1.5H). HR-MS(ESI, [M+H]+) m/z: 508.2075.

EXAMPLE 5: PREPARATION OF 4-(8-AMINO-3-((2S,3AR,6AS)-1-((E)-4-(DIMETHYLAMINO)BUT-2-ENOYL)HEXAHYDRO-1H-FURO [3,4-B]PYRROL-2-YL)IMIDAZO[1,5-A]PYRAZIN-1-YL)-N-(PYRIDIN-2-YL)BENZAMIDE (COMPOUND I-2)

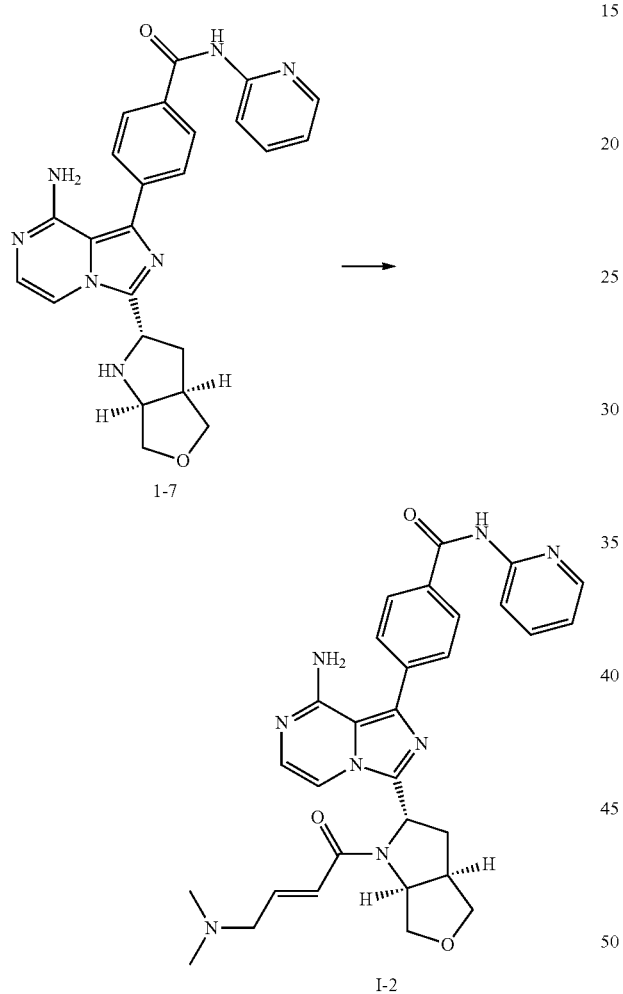

HATU (31.6 mg) was added to a stirred solution of intermediate 1-7 (50 mg), (E)-4-(dimethylamino)but-2-enoic acid hydrochloride (13.91 mg) and triethylamine (0.046 mL) in DCM (20 mL) in an ice bath, and after 5 min, the mixture was stirred in an ice bath for 5 min. After the reaction was completed, the reaction solution was added with water (20 mL) and DCM ((20 mL)). The organic phase was retained, washed with saturated sodium chloride solution (20 mL), and concentrated to remove the solvent, and the concentrate was purified by column chromatography to give compound I-2 (15 mg).

$^1$H NMR (500 MHz, DMSO-d6): δ 10.79 (s, 1H), 8.42-8.39 (m, 1H), 8.23-8.21 (m, 1H), 8.15-8.14 (m, 2H), 7.88-7.82 (m, 1.5H), 7.79-7.76 (m, 0.5H), 7.75-7.71 (m, 1H), 7.70-7.66 (m, 1H), 7.19-7.17 (m, 2H), 7.12-7.11 (m, 0.5H), 6.60-6.54 (m, 1H), 6.44-6.37 (m, 1H), 6.32-6.26 (m, 1H), 6.18-6.13 (m, 0.5H), 6.12-6.06 (m, 1H), 6.0-5.96 (m, 0.5H), 5.71-5.67 (m, 0.5H), 5.35-5.31 (m, 1H), 4.88-4.84 (m, 0.5H), 4.77-4.73 (m, 0.5H), 4.44-4.39 (m, 1H), 3.93-3.83 (m, 1.5H), 3.77-3.67 (m, 1.5H), 3.58-3.53 (m, 0.5H), 3.07-3.01 (m, 1H), 2.38-2.35 (m, 0.5H), 2.28-2.23 (0.5H), 2.17-2.12 (m, 0.5H). HR-MS(ESI, [M+H]+) m/z: 553.2665.

EXAMPLE 6: PREPARATION OF 4-(3-((2S,3AR,6AS)-1-ACRYLOYLHEXAHYDRO-1H-FURO[3,4-B]PYRROL-2-YL)-8-AMINOIMIDAZO [1,5-A]PYRAZIN-1-YL)-N-(PYRIDIN-2-YL)BENZAMIDE (COMPOUND I-3)

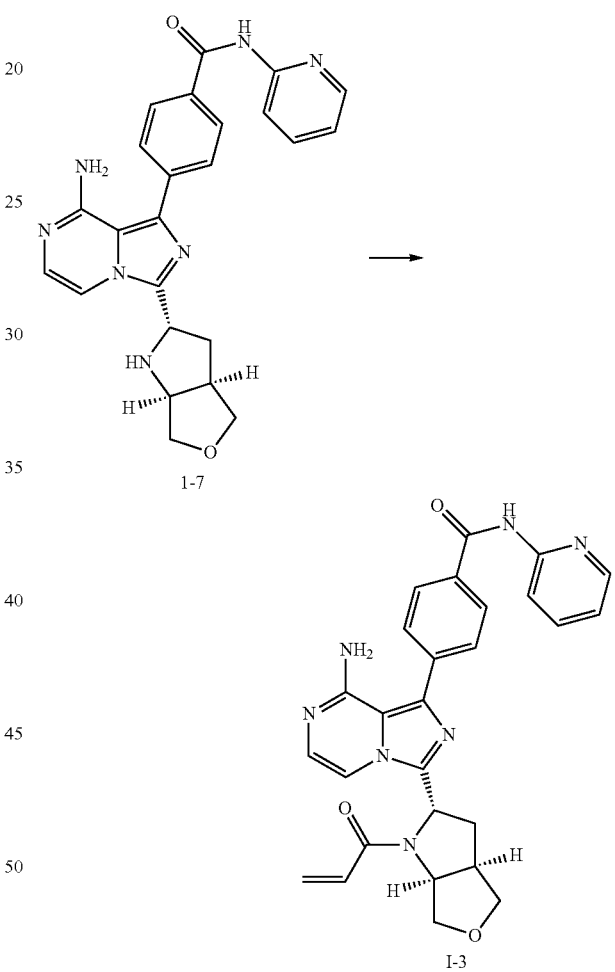

HATU (31.9 mg) was added dropwise to a stirred solution of intermediate 1-7 (50 mg), acrylic acid (6.11 mg) and TEA (0.046 mL) in DCM (10 mL) in an ice bath, and the mixture was stirred for 5 min in an ice bath after the addition. After the reaction was completed, the reaction solution was diluted with water (10 mL) and extracted with DCM (10 mL×3). The organic phases were combined, concentrated to remove the solvent, and the concentrate was dissolved in DCM (2 mL) and separated by preparative TLC to give compound I-3 (6 mg).

$^1$H NMR (500 MHz, DMSO-d6): δ 10.79 (s, 1H), 8.41-8.40 (m, 1H), 8.23-8.21 (m, 1H), 8.15-8.14 (m, 2H), 7.86-

7.84 (m, 1.5H), 7.74-7.7.69 (m, 2H), 7.19-7.17 (m, 1.5H), 7.13-7.12 (m, 0.5H), 6.55-6.48 (m, 0.5H), 6.33-6.35 (m, 0.5H), 6.22-6.15 (m, 1H), 6.15-6.06 (m, 1.5H), 6.06-6.0 (m, 1H), 5.73-5.67 (m, 1H), 5.51-5.47 (m, 0.5H), 5.35-5.31 (m, 0.5H), 4.92-4.87 (m, 0.5H), 4.79-4.73 (m, 0.5H), 3.94-3.86 (m, 1H), 3.78-3.66 (m, 1.5H), 3.55-3.51 (m, 0.5H), 3.41-3.38 (m, 0.5H), 3.03-2.94 (m, 1H), 2.31-2.21 (m, 1H), 2.20-2.12 (m, 0.5H), 2.04-1.95 (m, 1H). HR-MS(ESI, [M+H]+) m/z: 496.2065.

EXAMPLE 7: 4-(8-AMINO-3-((2S,3AR,6AS)-1-(BUT-2-YNOYL)HEXAHYDRO-1H-FURO[3,4-B]PYRROL-2-YL)IMIDAZO[1,5-A]PYRAZIN-1-YL)-3-FLUORO-N-(4-(TRIFLUOROMETHYL)PYRIDIN-2-YL)BENZAMIDE (COMPOUND I-4) AND 4-(3-((2S,3AR,6AS)-1-ACETYLHEXAHYDRO-1H-FURO[3,4-B]PYRROL-2-YL)-8-AMINOIMIDAZO[1,5-A]PYRAZIN-1-YL)-3-FLUORO-N-(4-(TRIFLUOROMETHYL)PYRIDIN-2-YL) BENZAMIDE (COMPOUND I-5)

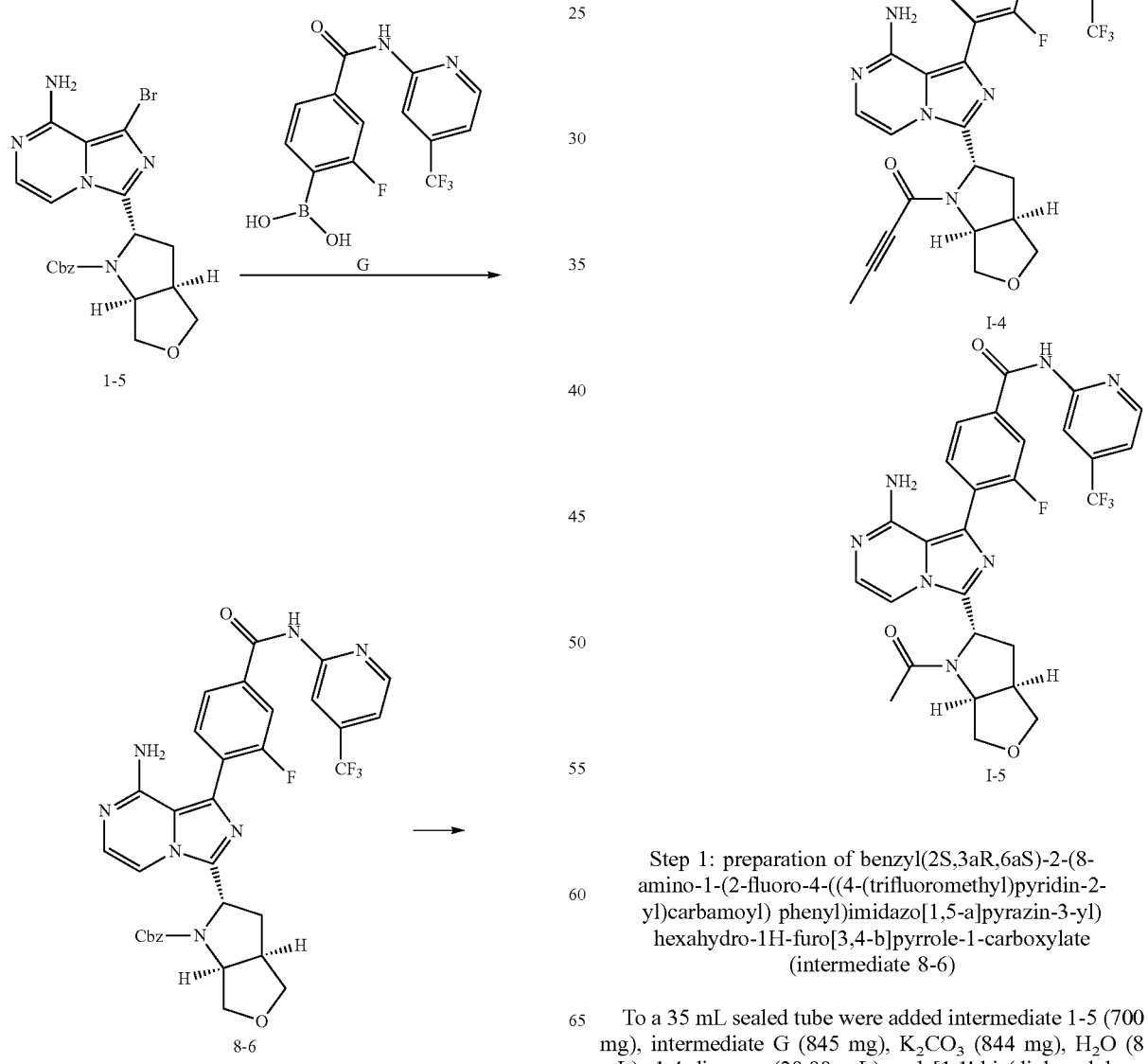

Step 1: preparation of benzyl(2S,3aR,6aS)-2-(8-amino-1-(2-fluoro-4-((4-(trifluoromethyl)pyridin-2-yl)carbamoyl) phenyl)imidazo[1,5-a]pyrazin-3-yl) hexahydro-1H-furo[3,4-b]pyrrole-1-carboxylate (intermediate 8-6)

To a 35 mL sealed tube were added intermediate 1-5 (700 mg), intermediate G (845 mg), K₂CO₃ (844 mg), H₂O (8 mL), 1,4-dioxane (20.00 mL) and [1,1'-bis(diphenylphosphino)ferrocene]dichloropalladium(II) dichloromethane complex (312 mg) sequentially. The mixture was bubbled with N₂ for 10 min, placed in a microwave reactor (50 W), and reacted at 80° C. for 20 min. After the reaction was detected by TLC, the reaction mixture was supplemented with [1,1'-bis (diphenylphosphino)ferrocene]palladium(II) dichloride dichloromethane complex (312 mg) and (2-fluoro-4-((4-(trifluoromethyl)pyridin-2-yl)carbamoyl) phenyl) boric acid (845 mg), and reacted for another 20 min in the microwave reactor. After the reaction was completed, the reaction solution was filtered, and the filtrate was added with water (20 mL) and extracted with EA (50 mL×3). The organic phases were combined, washed with saturated sodium chloride solution (100 mL×2), dried over anhydrous sodium sulfate, filtered and concentrated to remove the solvent, and the concentrate was separated by column chromatography to give intermediate 8-6 (0.38 g).

¹H NMR (500 MHz, DMSO-d6): δ 11.43 (s, 1H), 8.72-8.71 (m, 1H), 8.57 (s, 1H), 8.03-8.02 (m, 2H), 7.67-7.52 (m, 3H), 7.30 (s, 2H), 7.17-7.10 (m, 3H), 6.77-6.76 (m, 1H), 6.03 (s, 2H), 5.67-5.52 (m, 1H), 5.04-4.97 (m, 2H), 4.79-4.57 (m, 1H), 4.02-3.91 (m, 1H), 3.56-3.71 (m, 3H), 3.27-3.09 (m, 1H), 2.29-2.10 (m, 2H). HR-MS(ESI, [M+H]+) m/z: 662.4.

Step 2: preparation of 4-(8-amino-3-((2S,3aR,6aS)-hexahydro-1H-furo[3,4-b]pyrrol-2-yl)imidazo[1,5-a]pyrazin-1-yl)-3-fluoro-N-(4-(trifluoromethyl)pyridin-2-yl)benzamide (intermediate 8-7)

A solution of HBr (33%, 36.4 mmol) in acetic acid was slowly added dropwise to intermediate 8-6 (0.38 g) at room temperature, and the mixture was stirred at room temperature for 1 h. After the reaction was completed, the reaction solution was poured into water (50 mL) and extracted with DCM (20 mL×1). The aqueous phase was retained, adjusted to pH 11-14 with 2 M sodium hydroxide solution, and extracted with DCM (20 mL×3). The organic phases were combined, washed with saturated sodium chloride solution (20 mL×2), dried over anhydrous sodium sulfate, filtered and concentrated to give intermediate 8-7 (0.35 g).

¹H NMR (500 MHz, DMSO-d6): δ 8.69 (d, J=5 Hz, 1H), 8.54 (s, 1H), 8.03-8.01 (m, 2H), 7.79 (d, J=5 Hz, 1H), 7.64-7.61 (m, 1H), 7.54 (d, J=4.5 Hz, 1H), 7.08 (d, J=5 Hz, 1H), 6.0 (s, 2H), 4.64-4.61 (m, 1H), 3.96-3.95 (m, 1H), 3.76-3.70 (m, 1H), 3.67-3.61 (m, 2H), 2.94-2.87 (m, 1H), 2.29-2.27 (m, 1H), 2.01-1.97 (m, 2H). MS(ESI, [M–H]+) m/z: 526.4.

Step 3: Preparation of Compound I-4 and Compound I-5

To a reaction flask were added intermediate 8-7 (100 mg), HATU (55.1 mg), triethylamine (65.2 mg) and DCM (10 mL) sequentially, and the mixture was added dropwise with a solution of but-2-ynoic acid (2.71 mg) in DCM (3 mL) in an ice bath. After the reaction was completed, the reaction solution was diluted with water (20 mL) and extracted with DCM (20 mL×3). The organic phases were combined, washed twice with saturated brine, and concentrated to remove the solvent, and the concentrate was dissolved in DCM (2 mL) and purified by preparative TLC to give compound I-4 (11 mg) and compound I-5 (8 mg).

Compound I-4:
¹H NMR (500 MHz, DMSO-d6): δ 11.44 (br, 1H), 8.72-8.71 (m, 1H), 8.56 (s, 1H), 8.04-8.01 (m, 2H), 7.89-7.78 (m, 1H), 7.65-7.64 (m, 1H), 7.58-7.57 (m, 1H), 7.16-7.11 (m, 1H), 6.09-6.05 (m, 2H), 5.89-5.64 (m, 0.5H), 5.33-5.32 (m, 0.5H), 4.80-4.59 (m, 1H), 4.03-3.81 (m, 2H), 3.77-3.58 (m, 3H), 2.27-2.14 (m, 2H), 1.66-1.48 (m, 1.5H), 1.46-1.45 (m, 1.5H). MS(ESI, [M–H]+) m/z: 592.4.

Compound I-5:
¹H NMR (500 MHz, DMSO-d6): δ 11.44 (br, 1H), 8.72-8.71 (m, 1H), 8.55 (s, 1H), 8.02-7.78 (m, 2H), 7.29-7.20 (m, 1H), 7.66-7.65 (m, 1H), 7.65-7.63 (m, 1H), 7.58-7.57 (m, 1H), 7.17-7.10 (m, 1H), 6.11-6.05 (m, 0.5H), 6.03-5.98 (m, 0.5H), 5.79-5.61 (m, 0.5H), 4.72 (s, 0.5H), 4.59 (s, 0.5H), 4.45 (s, 0.5H), 3.88-3.83 (m, 2H), 3.74-3.63 (m, 3H), 2.22-2.13 (m, 2H), 2.01-2.00 (m, 1H), 1.99-1.46 (m, 2H). MS(ESI, [M–H]+) m/z: 568.4.

EXAMPLE 8: PREPARATION OF 4-(3-((2S,3AR, 6AS)-1-ACRYLOYLHEXAHYDRO-1H-FURO[3, 4-B]PYRROL-2-YL)-8-AMINOIMIDAZO [1,5-A] PYRAZIN-1-YL)-3-FLUORO-N-(4-(TRIFLUOROMETHYL)PYRIDIN-2-YL) BENZAMIDE (COMPOUND I-6)

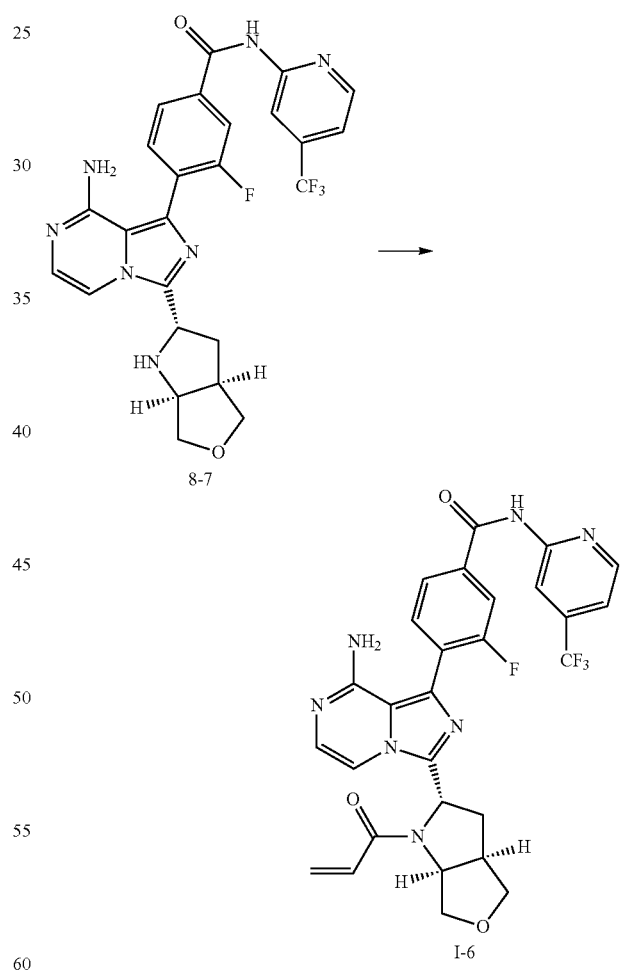

To a reaction flask were added intermediate 8-7 (100 mg), TEA (0.069 mL) and DCM (20 mL), then a solution of acrylic acid (13.66 mg) in DCM (1 mL) was added slowly, followed by a solution of T₃P (50%, 0.19 mmol) in ethyl acetate (121 mg). The mixture was stirred at room temperature for 2 h. After the reaction was completed, the reaction solution was concentrated, and the concentrate was added with water (20 mL) and DCM (20 mL). The aqueous phase was extracted with DCM (20 mL×2), and the organic phases were combined, washed twice with saturated brine, dried over anhydrous sodium sulfate and filtered, the filtrate was concentrated, and the concentrate was purified by preparative TLC to give compound I-6 (10 mg).

¹H NMR (500 MHz, DMSO-d6): δ 11.45 (br, 1H), 8.72-8.71 (m, 1H), 8.55 (s, 1H), 8.02 (s, 2H), 7.79-7.72 (m, 1H), 7.66-7.63 (m, 1H), 7.58-7.57 (m, 1H), 7.17-7.10 (m, 1H), 6.10-5.99 (m, 2H), 5.78-5.60 (m, 0.5H), 4.72-4.59 (m, 0.5H), 4.59-4.45 (m, 1H), 3.88-3.83 (m, 2H), 3.74-3.63 (m, 3H), 2.22-2.13 (m, 2H), 2.01-2.00 (m, 1H), 1.99-1.46 (m, 2H). MS(ESI, [M+H]⁺) m/z: 582.3.

EXAMPLE 9: PREPARATION OF 4-(8-AMINO-3-((2S,3AR,6AS)-1-(CYCLOPROPANECARBONYL)HEXAHYDRO-1H-FURO[3,4-B]PYRROL-2-YL)IMIDAZO[1,5-A]PYRAZIN-1-YL)-3-FLUORO-N-(4-(TRIFLUOROMETHYL)PYRIDIN-2-YL)BENZAMIDE (COMPOUND I-7)

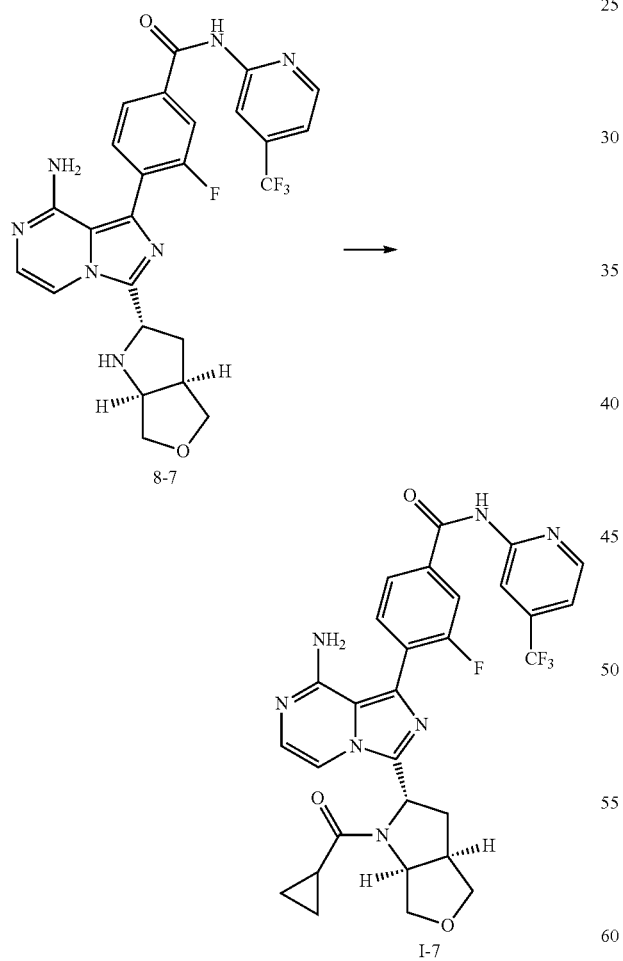

To a reaction flask were added intermediate 8-7 (68 mg), HATU (41.7 mg), TEA (0.076 mL) and DCM (6 mL), then a solution of cyclopropanecarboxylic acid (8.58 mg) in DCM (2 mL) was slowly added, and the mixture was reacted for 10 min in an ice bath. After the reaction was completed, the reaction solution was added with water (10 mL) and extracted with DCM (20 mL×3). The organic phases were combined, washed twice with saturated sodium chloride solution and concentrated, and the concentrate was purified by preparative TLC to give compound I-7 (11 mg).

¹H NMR (500 MHz, DMSO-d6): δ 8.72-8.71 (m, 1H), 8.56 (s, 1H), 8.03-8.00 (m, 2H), 7.80-7.74 (m, 1H), 7.64-7.61 (m, 1H), 7.58-7.57 (m, 1H), 7.14-7.13 (m, 0.5H), 7.08-7.07 (m, 0.5H), 6.07-6.04 (m, 1.5H), 5.98 (s, 1H), 4.95-4.90 (m, 0.5H), 4.65-4.60 (m, 0.5H), 3.81-3.73 (m, 1H), 3.72-3.65 (m, 1H), 3.64-3.59 (m, 0.5H), 3.55-3.49 (m, 0.5H), 3.44-3.38 (m, 1H), 2.95-2.99 (m, 0.5H), 3.02-2.94 (m, 0.5H), 2.29-2.23 (m, 1H), 2.23-2.18 (m, 0.5H), 2.18-2.10 (m, 0.5H), 2.04-1.95 (m, 1H), 1.71-1.63 (m, 0.5H), 1.52-1.43 (m, 1H), 0.88-0.73 (m, 2H), 0.73-0.60 (m, 1.5H), 0.60-0.52 (m, 0.5H). MS(ESI, [M+H]+) m/z: 596.4.

EXAMPLE 10: PREPARATION OF 4-(8-(CYCLOPROPYLSULFONYLAMINO)-3-((2S,3AR,6AS)-HEXAHYDRO-1H-FURO[3,4-B]PYRROL-2-YL)IMIDAZO[1,5-A]PYRAZIN-1-YL)-3-FLUORO-N-(4-(TRIFLUOROMETHYL)PYRIDIN-2-YL)BENZAMIDE (COMPOUND I-8)

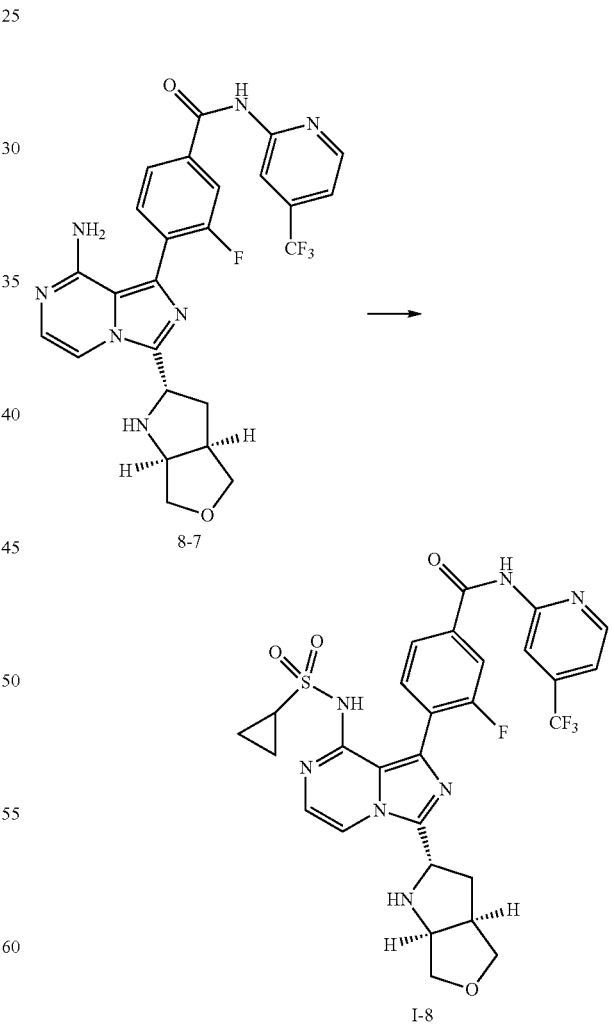

To a reaction flask were added intermediate 8-7 (0.12 g) and DCM (10 mL), then cyclopropanesulfonyl chloride (0.29 g), DMAP (0.028 g) and DIPEA (0.074 g) were added at 0° C., and the mixture was heated to reflux after the addition. After the reaction was completed, the reaction solution was added with water (10 mL) and extracted with DCM. The organic phase were dried over anhydrous sodium sulfate, filtered, concentrated and purified by preparative TCL to give compound I-8 (0.015 g). ¹H NMR (500 MHz, DMSO) δ 11.43 (s, 1H), 8.72-8.71 (d, J=5 Hz, 1H), 8.57 (s, 1H), 7.98-7.94 (m, 2H), 7.81-7.80 (d, J=6 Hz, 1H), 7.68-7.65 (m, 1H), 7.58-7.57 (d, J=5 Hz, 2H), 6.85-6.84 (d, J=6 Hz, 1H), 5.33 (m, 1H), 4.66 (m, 1H), 3.99 (m, 1H), 3.75-3.64 (m, 4H), 2.94 (s, 1H), 2.02-1.99 (m, 2H), 1.48-1.45 (m, 1H), 0.87-0.80 (m, 4H). MS(ESI, [M+H]+) m/z: 632.3.

EXAMPLE 11: PREPARATION OF 4-(8-AMINO-3-((2S,3AR,6AS)-1-(N-ISOPROPYLSULFA-MOYL)HEXAHYDRO-1H-FURO[3,4-B]PYR-ROL-2-YL)IMIDAZO[1,5-A]PYRAZIN-1-YL)-3-FLUORO-N-(4-(TRIFLUOROMETHYL) PYRIDIN-2-YL)BENZAMIDE (COMPOUND 1-9)

¹H NMR (500 MHz, DMSO) δ 11.43 (s, 1H), 8.72-8.71 (d, J=5 Hz, 1H), 8.57 (s, 1H), 8.06-8.02 (m, 2H), 7.72-7.71 (m, 1H), 7.67-7.64 (m, 1H), 7.59-7.58 (d, J=5 Hz, 1H), 7.12-7.11 (m, 1H), 6.79-6.78 (m, 1H), 6.04 (s, 2H), 5.45-5.44 (m, 1H), 4.43-4.42 (m, 1H), 4.16-4.14 (m, 1H), 3.70-3.69 (m, 1H), 3.58-3.49 (m, 3H), 3.06-3.04 (m, 1H), 2.26 (s, 1H), 2.13 (s, 1H), 0.96-0.89 (m, 6H). MS(ESI, [M+H]+) m/z: 649.4.

EXAMPLE 12: PREPARATION OF 4-(8-AMINO-3-((2S,3AR,6AS)-1-(2-HYDROXYACETYL) HEXAHYDRO-1H-FURO[3,4-B]PYRROL-2-YL) IMIDAZO[1,5-A]PYRAZIN-1-YL)-3-FLUORO-N-(4-(TRIFLUOROMETHYL)PYRIDIN-2-YL) BENZAMIDE (COMPOUND I-10)

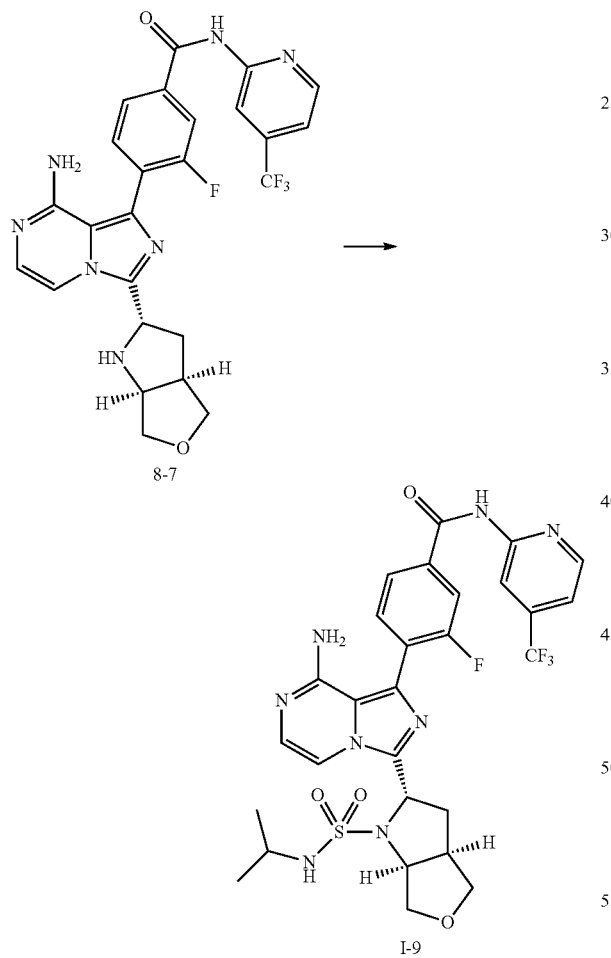

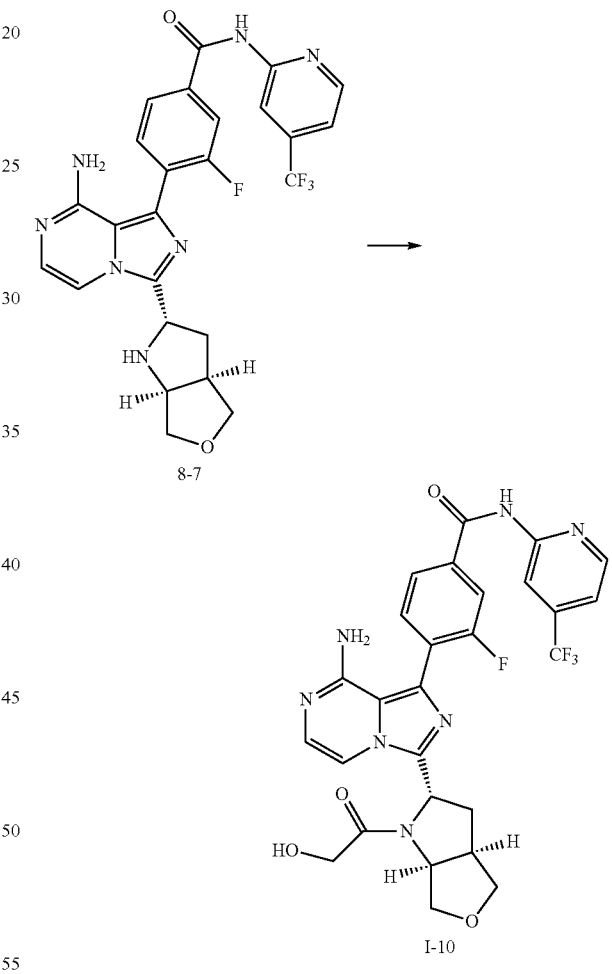

To a reaction flask were added intermediate 8-7 (0.10 g) and DCM (10 mL), then N-isopropylaminosulfonyl chloride (0.028 g) and triethylamine (0.077 g) were added at 0° C., and the mixture was reacted at room temperature. After the reaction was completed, the reaction solution was added with water (10 mL) and extracted with DCM. The organic phase was dried over anhydrous sodium sulfate, filtered, concentrated, and purified by YMC HPLC to give compound I-9 (0.068 g).

To a reaction flask was added intermediate 8-7 (0.060 g) and DCM (10 mL), then glycolic acid (0.052 g), DMAP (0.028 g) and DIPEA (0.029 g) were added at 0° C. The mixture was stirred for 5 min in an ice bath, added with HATU (0.45 g), and heated to reflux for 48 h. Then the reaction solution was added with water (10 mL) and extracted with DCM. The organic phase was dried over anhydrous sodium sulfate, filtered, concentrated and purified by preparative TLC to give compound I-10 (0.029 g).

¹H NMR (500 MHz, DMSO) δ 11.44 (s, 1H), 8.72-8.71 (d, J=5 Hz, 1H), 8.56 (s, 1H), 8.23-8.21 (d, J=7 Hz, 1H), 8.04-8.01 (m, 2H), 7.75-7.64 (m, 1H), 7.59-7.58 (d, J=5 Hz, 2H), 6.31 (s, 2H), 5.69-5.85 (m, 1H), 4.77 (m, 2H), 4.65 (m, 1H), 3.80 (s, 1H), 3.73-3.52 (m, 4H), 2.23-2.21 (d, J=7.5 Hz, 2H), 2.05 (m, 1H). MS(ESI, [M+H]+) m/z: 586.3.

EXAMPLE 13: PREPARATION OF 4-(8-AMINO-3-((2S,3AR,6AS)-1-(1-HYDROXYCYCLOPROPANE-1-CARBONYL)HEXAHYDRO-1H-FURO[3,4-B]PYRROL-2-YL)IMIDAZO[1,5-A]PYRAZIN-1-YL)-3-FLUORO-N-(4-(TRIFLUOROMETHYL)PYRIDIN-2-YL)BENZAMIDE (COMPOUND I-11)

Hz, 1H), 2.22-2.18 (m, 2H), 1.09-1.08 (d, J=8 Hz, 1H), 0.94-0.82 (m, 2H), 0.16-0.12 (m, 1H). MS(ESI, [M+H]+) m/z: 612.4.

EXAMPLE 14: PREPARATION OF 4-(8-AMINO-3-((2S,3AR,6AS)-1-(CYCLOBUTYLCARBONYL)HEXAHYDRO-1H-FURO[3,4-B]PYRROL-2-YL)IMIDAZO[1,5-A]PYRAZIN-1-YL)-3-FLUORO-N-(4-(TRIFLUOROMETHYL)PYRIDIN-2-YL)BENZAMIDE (COMPOUND I-12)

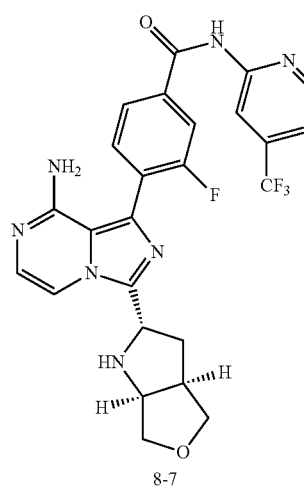

8-7

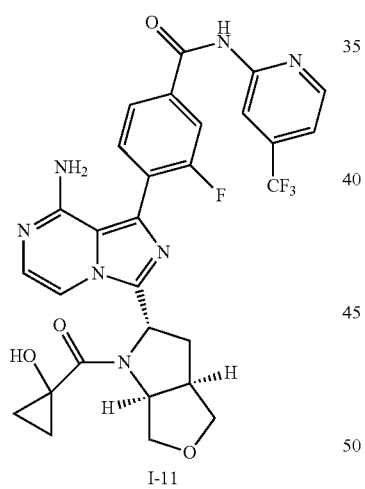

I-11

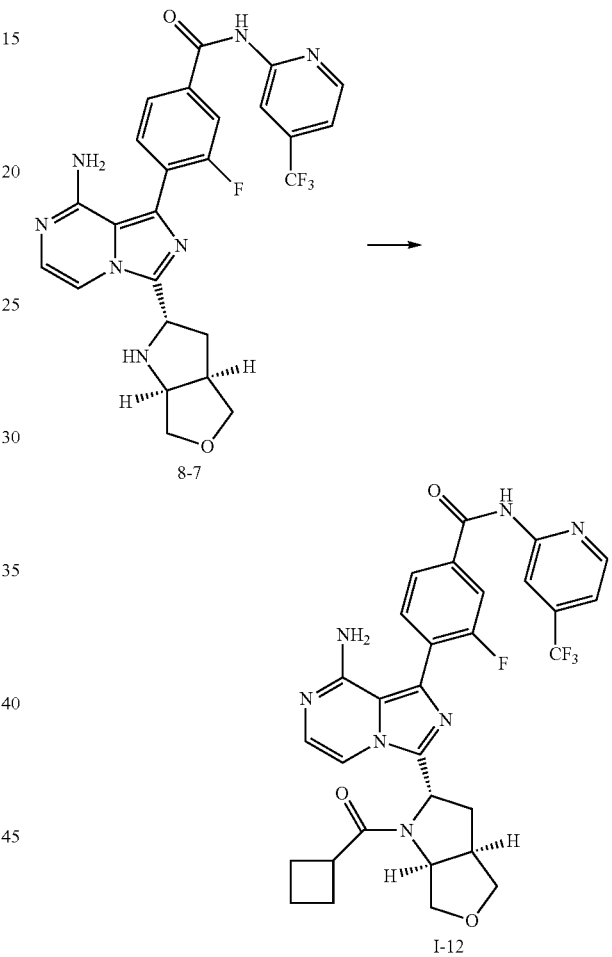

To a reaction flask were added intermediate 8-7 (0.15 g) and DCM (15 mL), then 1-hydroxycyclopropane-1-carboxylic acid (0.028 g) and triethylamine (0.058 g) were added at 0° C., and the mixture was stirred for 5 min in an ice bath, added with HATU (0.11 g), and heated to reflux for 24 h. Then the reaction solution was added with water (10 m) and extracted with DCM. The organic phase was dried over anhydrous sodium sulfate, filtered, concentrated, and purified by YMC HPLC to give compound I-11 (0.045 g).

$^1$H NMR (500 MHz, DMSO) δ 11.42 (s, 1H), 8.71 (s, 1H), 8.56 (s, 1H), 8.03-8.01 (d, J=9 Hz, 2H), 7.82-7.58 (m, 3H), 7.09 (s, 1H), 6.22-6.19 (d, J=13 Hz, 1H), 6.03-6.01 (d, J=8.5 Hz, 2H), 5.70-5.15 (m, 1H), 4.70-4.01 (m, 1H), 3.81-3.77 (m, 1H), 3.74-3.64 (m, 2H), 3.54 (s, 1H), 3.38-3.37 (d, J=7.5

To a reaction flask were added intermediate 8-7 (180 mg) and DCM (20 mL), then Et$_3$N (0.19 mL) and HATU (143 mg) were added while stirring, and the mixture was purged with nitrogen three times, added with a solution of cyclobutanecarboxylic acid (34.2 mg) in DCM in portions at −20° C., and reacted at room temperature overnight after the addition. The reaction solution was added with water, and the aqueous phase was extracted with DCM. The organic phases were combined, washed with saturated brine, dried over anhydrous magnesium sulfate, filtered and purified by silica gel column chromatography (eluent: DCM-MeOH (99:1 to 95:5)) to give compound I-12 (50 mg).

$^1$H NMR (500 MHz, DMSO-d6) δ 11.39 (d, J=5.8 Hz, 1H), 8.70 (d, J=4.9 Hz, 1H), 8.54 (s, 1H), 8.08-7.93 (m, 2H), 7.76 (dd, J=22.6, 4.9 Hz, 1H), 7.64-7.52 (m, 2H), 7.14 (dd, J=35.1, 4.8 Hz, 1H), 6.04 (d, J=32.4 Hz, 2H), 5.68 (d, J=62.2

Hz, 1H), 4.69-4.57 (m, 1H), 3.90-3.83 (m, 1H), 3.73-3.62 (m, 4H), 3.22-3.15 (m, 1H), 3.06-2.98 (m, 1H), 2.96-2.88 (m, 1H), 2.19-2.06 (m, 2H), 2.05-1.92 (m, 1H), 1.87 (dd, J=18.6, 9.4 Hz, 1H), 1.68 (dd, J=16.0, 8.3 Hz, 1H), 1.62-1.54 (m, 1H). HR-MS(ESI, [M+H]$^+$) m/z: 610.2185.

EXAMPLE 15: PREPARATION OF 4-(8-AMINO-3-((2S,3AR,6AS)-1-(N,N-DIMETHYLSULFAMOYL)HEXAHYDRO-1H-FURO [3,4-B]PYRROL-2-YL)IMIDAZO[1,5-A]PYRAZIN-1-YL)-3-FLUORO-N-(4-(TRIFLUOROMETHYL)PYRIDIN-2-YL)BENZAMIDE (COMPOUND I-13)

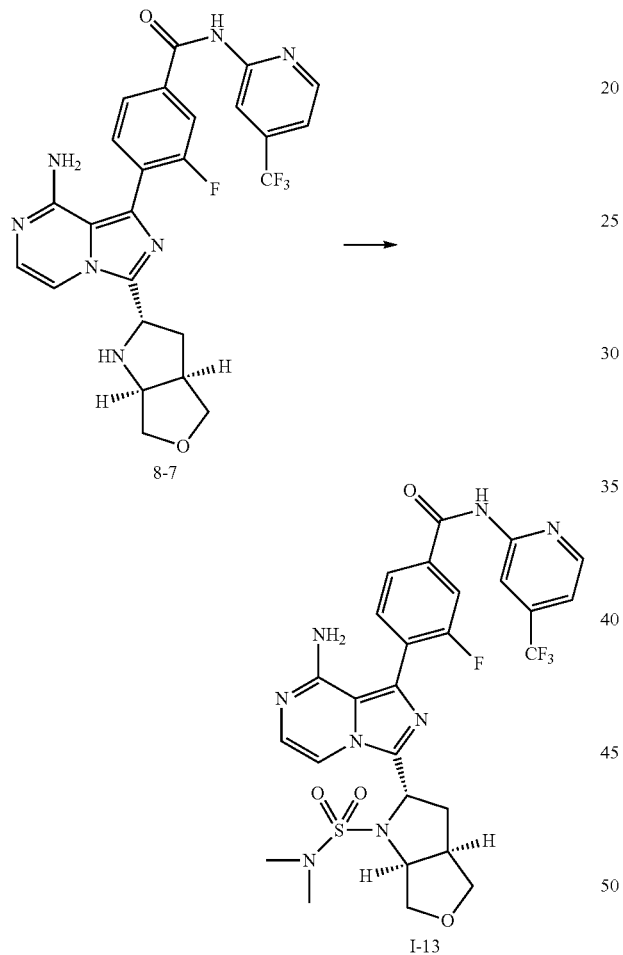

1H), 3.61 (d, J=9.2 Hz, 2H), 3.52-3.42 (m, 1H), 2.40 (s, 6H), 2.18 (dd, J=13.3, 6.7 Hz, 1H), 2.05-1.94 (m, 1H). HR-MS (ESI, [M+H]+) m/z: 635.1808.

EXAMPLE 16: PREPARATION OF DIMETHYL (1-(2-FLUORO-4-((4-(TRIFLUOROMETHYL)PYRIDIN-2-YL)CARBAMOYL)PHENYL)-3-((2S,3AR,6AS)-HEXAHYDRO-1H-FURO[3,4-B]PYRROL-2-YL)IMIDAZO[1,5-A]PYRAZIN-8-YL)PHOSPHATE (COMPOUND 1-14)

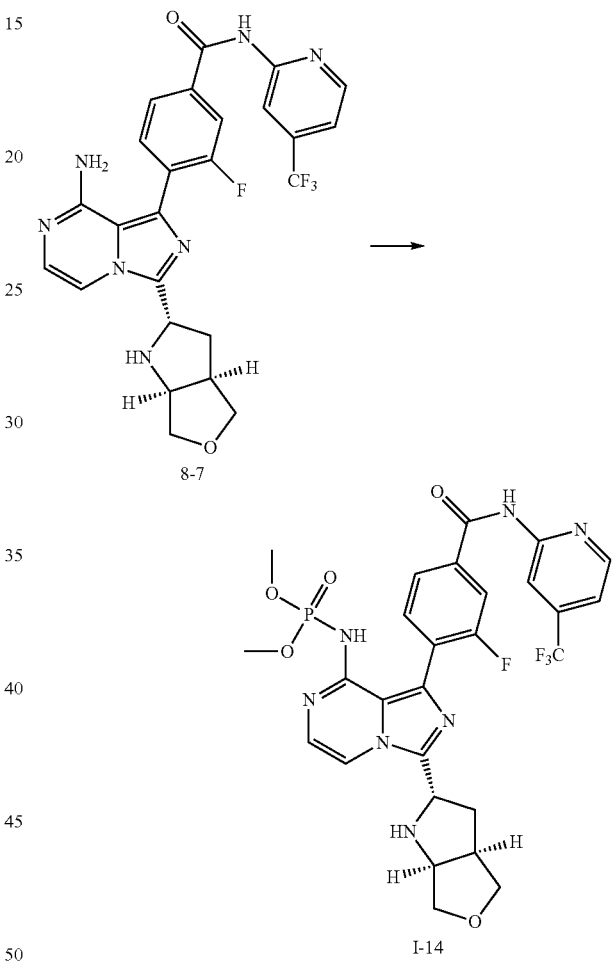

To a reaction flask were added intermediate 8-7 (150 mg) and Py (10 mL), then dimethylsulfamoyl chloride (82 mg) was slowly added in an ice-water bath under nitrogen atmosphere. The mixture was heated to 35° C. and reacted for 48 h after the addition. The reaction solution was concentrated, and the concentrate was dissolved in DCM-MeOH (10:1) and purified by preparative TLC to give compound I-13 (30 mg).

$^1$H NMR (500 MHz, DMSO-d6) δ 11.44 (s, 1H), 8.72 (d, J=4.5 Hz, 1H), 8.57 (s, 1H), 8.04 (t, J=8.7 Hz, 2H), 7.76 (d, J=4.4 Hz, 1H), 7.66 (t, J=7.5 Hz, 1H), 7.58 (d, J=4.6 Hz, 1H), 7.13 (d, J=4.4 Hz, 1H), 6.11 (s, 2H), 5.46 (d, J=5.8 Hz, 1H), 4.51 (s, 1H), 4.07 (d, J=10.1 Hz, 1H), 3.71 (d, J=8.9 Hz,

To a reaction flask were added intermediate 8-7 (100 mg), DMAP (2.32 mg), DIPEA (0.083 mL) and DCM (20 mL), then a solution of dimethyl chlorophosphate (27.4 mg) in DCM (1 mL) was slowly added, and the mixture was heated to reflux after the addition. After the reaction was completed, the reaction solution was washed twice with water. The organic phase was concentrated, and the concentrate was purified by YMC HPLC to give compound I-14 (20 mg).

$^1$H NMR (500 MHz, DMSO-d6): δ 11.42 (s, 1H), 10.65 (br, 1H), 8.71-8.70 (m, 1H), 8.55 (s, 1H), 7.95-7.91 (m, 2H), 7.70-7.69 (m, 1H), 7.66-7.63 (m, 1H), 7.57-7.56 (m, 1H), 6.87-6.86 (m, 1H), 5.33 (s, 1H), 4.63-4.60 (m, 1H), 3.75-3.72 (m, 1H), 3.63-3.64 (m, 3H), 3.39-3.37 (m, 6H), 2.91-2.92 (m, 1H), 2.31-2.25 (m, 1H), 2.03-1.99 (m, 2H). MS(ESI, [M+H]+) m/z: 636.4.

EXAMPLE 17: PREPARATION OF 4-(8-AMINO-3-((2S,3AR,6AS)-1-(N-METHYLSULFAMOYL)HEXAHYDRO-1H-FURO[3,4-B]PYRROL-2-YL)IMIDAZO[1,5-A]PYRAZIN-1-YL)-3-FLUORO-N-(4-(TRIFLUOROMETHYL)PYRIDIN-2-YL)BENZAMIDE (COMPOUND I-15)

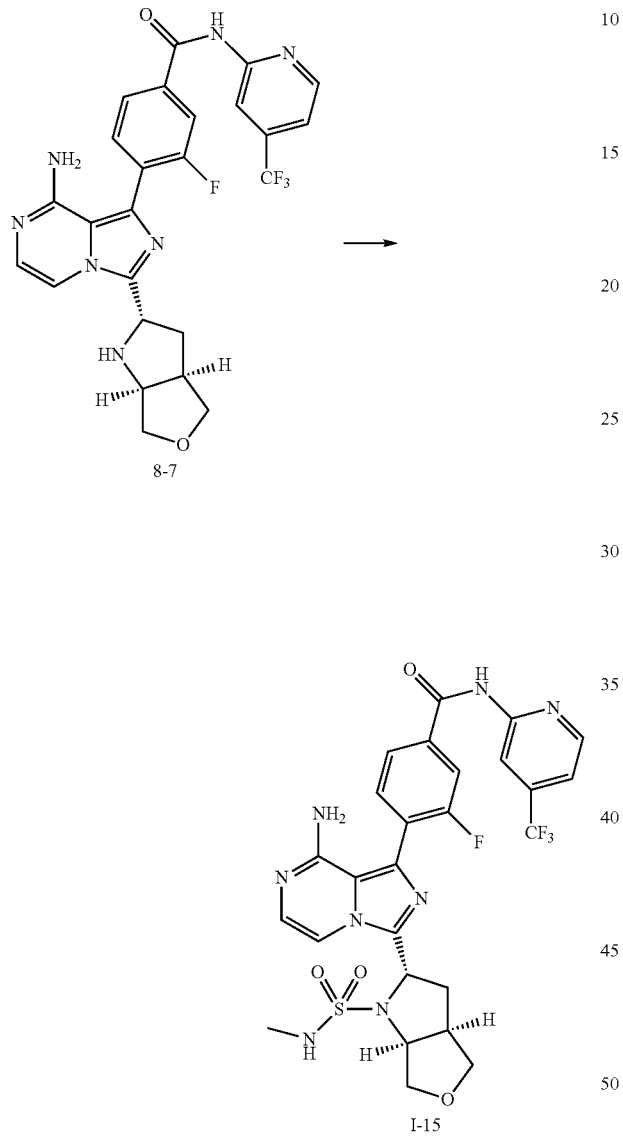

A solution of methylsulfamoyl chloride (35.0 mg) in DCM (1 mL) were slowly added to a stirred solution of intermediate 8-7 (150 mg) and triethylamine (115 mg) in dichloromethane (30 mL) at 0° C., and the stirring was continued for reaction after the addition. After the reaction was completed, the reaction solution was purified by column chromatography to give compound I-15 (50 mg).

$^1$H NMR (500 MHz, DMSO-d6): δ 11.42 (s, 1H), 8.72-8.71 (m, 1H), 8.56 (s, 1H), 8.04-8.01 (m, 2H), 7.74-7.31 (m, 1H), 7.66-7.64 (m, 1H), 7.58-7.57 (m, 1H), 7.11-7.10 (m, 1H), 6.79-7.79 (m, 1H), 6.01 (br, 2H), 5.44-5.42 (m, 1H), 4.47-4.39 (m, 1H), 4.10-4.07 (m, 1H), 3.70-3.58 (m, 1H), 3.57-3.50 (m, 2H), 2.27-2.27 (m, 1H), 2.25-2.21 (m, 3H), 2.01-1.99 (m, 1H). MS(ESI, [M+H]+) m/z: 621.4.

EXAMPLE 18: PREPARATION OF 4-(8-AMINO-3-((2S,3AR,6AS)-1-GLYCYLHEXAHYDRO-1H-FURO[3,4-B]PYRROL-2-YL)IMIDAZO [1,5-A]PYRAZIN-1-YL)-3-FLUORO-N-(4-(TRIFLUOROMETHYL)PYRIDIN-2-YL)BENZAMIDE (COMPOUND I-16)

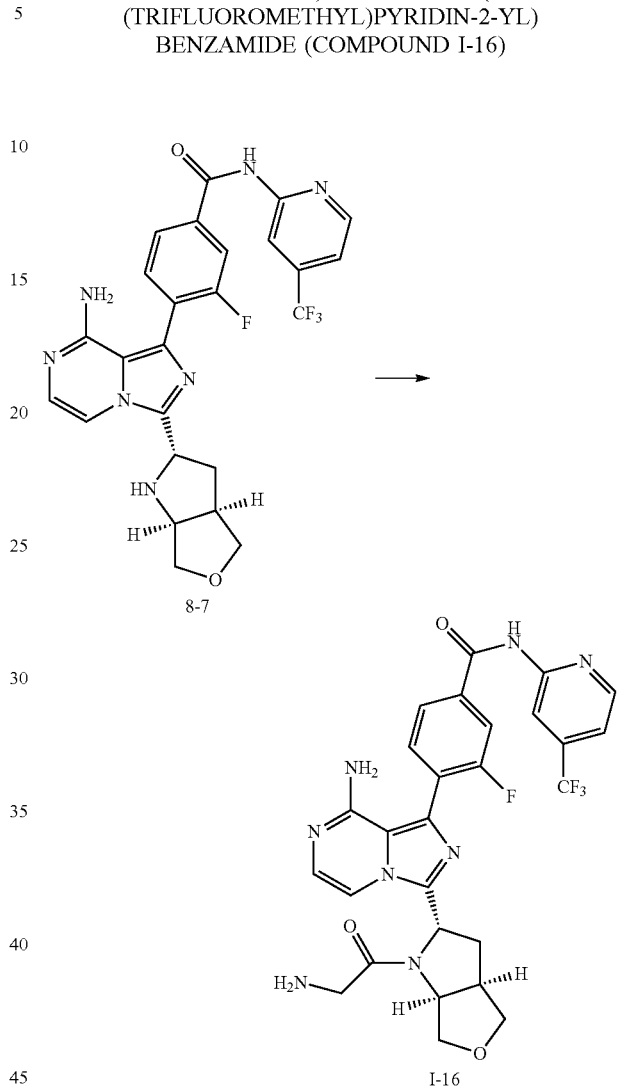

To a reaction flask were added intermediate 8-7 (200 mg), HATU (123 mg), triethylamine (130 mg) and DCM (10 mL) sequentially, then a solution of (tert-butoxycarbonyl)glycine (53.6 mg) in DCM (1 mL) was added dropwise in an ice bath. After the reaction was completed, the reaction solution was washed with water (20 mL×2). The organic phase was dried over anhydrous sodium sulfate, filtered and purified by column chromatography to give a solid compound. The solid compound was added to a solution of 4 M hydrogen chloride in methanol (10 mL), and the mixture was stirred vigorously. After the reaction was completed, the reaction solution was washed with saturated sodium bicarbonate solution (20 mL×2). The organic phase was dried over anhydrous sodium sulfate and filtered, the filtrate was concentrated, and the concentrate was purified by preparative TLC to give compound I-16 (30 mg).

$^1$H NMR (500 MHz, DMSO-d6): δ 8.72-8.71 (m, 1H), 8.55 (s, 1H), 8.04-8.00 (m, 2H), 7.86-7.82 (m, 0.5H), 7.73-7.69 (m, 0.5H), 7.69-7.61 (m, 1H), 7.60-7.54 (m, 1H), 7.23-7.16 (m, 0.5H), 7.14-7.09 (m, 0.5H), 6.27-5.92 (br,

2H), 5.95-5.86 (m, 1H), 5.73-5.66 (m, 1H), 4.78-4.60 (m, 1H), 3.94-3.86 (m, 1H), 3.84-3.79 (m, 1H), 3.78-3.73 (m, 1H), 3.72-3.66 (m, 0.5H), 3.66-3.61 (m, 0.5H), 3.52-3.47 (m, 2H), 3.00-2.91 (m, 1H), 2.30-2.19 (m, 2H), 2.05-1.95 (m, 1H). MS(ESI, [M+H]$^+$) m/z: 585.4.

EXPERIMENTAL EXAMPLE 1: IN VITRO ACTIVITY 1.1 Screening for BTK Inhibitory Activity 350 ng/µL BTK stock solution was diluted with kinase buffer (50 mM HEPES, 10 mM MgCl$_2$, 2 mM DTT, 1 mM EGTA, 0.01% Tween 20), and 6 µL of 1.67× working solution at 0.0334 ng/µL (final concentration: 0.02 ng/µL) was added to each well. Different compounds dissolved in DMSO were added to the wells using a nanoliter pipettor, resulting in the final concentration of 1000 nM to 0.244 nM (4-fold gradient for 7 concentrations in total), and blank control wells (without enzyme) and negative control wells (with enzyme, plus vehicle DMSO) were set, 2 replicate wells for each well. After enzyme was reacted with the compound or vehicle for 30 min, 5×ATP at 100 µM (final concentration: 20 µM) prepared with kinase buffer was mixed with 5×substrate at 0.5 µM (final concentration: 0.1 µM, ULight-poly GT) at a ratio of 1:1, and the mixture was added to each well at 4 µL/well. After being sealed with a film, the plate was incubated at room temperature for 2 h, then 5 µL of 4×EDTA at 40 mM (final concentration: 10 mM) was added to each well. After the plate was incubated for 5 min at room temperature, 5 µL of 4× detection reagent at 8 nM (final concentration: 2 nM, Ab) was added to each well, followed by incubation at room temperature for 1 h. The plate was read using a PE Envision multi-functional microplate reader (excitation: 620 nm, emission: 665 nm), and IC$_{50}$ was calculated by four-parameter fitting.

1.2 Screening for EGFR (Epidermal Growth Factor Receptor) Inhibitory Activity 50 ng/µL EGFR (WT) stock solution was diluted with kinase buffer (50 mM HEPES, 10 mM MgCl$_2$, 2 mM DTT, 1 mM EGTA, 0.01% Tween 20), and 6 µL of 1.67× working solution at 0.01336 ng/µL (final concentration: 0.008 ng/µL) was added to each well. Different compounds dissolved in DMSO were added to the wells using a nanoliter pipettor, resulting in the final concentration of 1000 nM to 0.48 nM (4-fold gradient for 7 concentrations in total), and blank control wells (without enzyme) and negative control wells (with enzyme, plus vehicle DMSO) were set, 2 replicate wells for each well. After enzyme was reacted with the compound or vehicle for 10 min, 5× ATP at 25 µM (final concentration: 5 µM) prepared with kinase buffer was mixed with 5× substrate at 0.5 µM (final concentration: 0.1 µM, ULight-poly GT) at a ratio of 1:1, and the mixture was added to each well at 4 µL/well. After being sealed with a film, the plate was incubated at room temperature for 2 h, then 5 µL of 4×EDTA at 40 mM (final concentration: 10 mM) was added to each well. After the plate was incubated for 5 min at room temperature, 5 µL of 4× detection reagent at 8 nM (final concentration: 2 nM, Eu-anti-phospho-tyrosine antibody) was added to each well, followed by incubation at room temperature for 1 h. The plate was read using a PE Envision multi-functional microplate reader (excitation: 320 nm, emission: 665 nm), and IC$_{50}$ was calculated by four-parameter fitting.

1.3 Screening for TEC Inhibitory Activity 50 ng/µL TEC stock solution was diluted with kinase buffer (50 mM HEPES, 10 mM MgCl$_2$, 2 mM DTT, 1 mM EGTA, 0.01% Tween 20), and 6 µL of 1.67× working solution at 0.01336 g/µL (final concentration: 0.008 ng/µL) was added to each well. Different compounds dissolved in DMSO were added to the wells using a nanoliter pipettor, resulting in the final concentration of 1000 nM to 0.24 nM (4-fold gradient for 7 concentrations in total), and blank control wells (without enzyme) and negative control wells (with enzyme, plus vehicle DMSO) were set. After enzyme was reacted with the compound or vehicle for 30 min, 5×ATP at 50 µM (final concentration: 10 µM) prepared with kinase buffer was mixed with 5× substrate at 0.5 µM (final concentration: 0.1 µM, ULight-poly GT) at a ratio of 1:1, and the mixture was added to each well at 4 µL/well. After being sealed with a film, the plate was incubated at room temperature for 2 h, then 5 µL of 4×EDTA at 40 mM (final concentration: 10 mM) was added to each well. After the plate was incubated for 5 min at room temperature, 5 µL of 4× detection reagent at 8 nM (final concentration: 2 nM, Eu-anti-phospho-tyrosine antibody) was added to each well, followed by incubation at room temperature for 1 h. The plate was read using a PE Envision multi-functional microplate reader (excitation: 320 nm, emission: 665 nm), and IC$_{50}$ was calculated by four-parameter fitting.

1.4 Screening for ITK (Interleukin-2-Inhibitor T-Cell Kinase) Inhibition Activity 50 ng/µL ITK stock solution was diluted with kinase buffer (50 mM HEPES, 10 mM MgCl$_2$, 2 mM DTT, 1 mM EGTA, 0.01% Tween 20), and 6 µL of 1.67× working solution at 0.0835 g/µL (final concentration: 0.05ng/µL) was added to each well. Different compounds dissolved in DMSO were added to the wells using a nanoliter pipettor, resulting in the final concentration of 1000 nM to 0.24 nM (4-fold gradient for 7 concentrations in total), and blank control wells (without enzyme) and negative control wells (with enzyme, plus vehicle DMSO) were set. After enzyme was reacted with the compound or vehicle for 30 min, 5×ATP at 50 µM (final concentration: 10 µM) prepared with kinase buffer was mixed with 5× substrate at 0.5 µM (final concentration: 0.1 µM, ULight-poly GT) at a ratio of 1:1, and the mixture was added to each well at 4 µL/well. After being sealed with a film, the plate was incubated at room temperature for 2 h, then 5 µL of 4×EDTA at 40 mM (final concentration: 10 mM) was added to each well. After the plate was incubated for 5 min at room temperature, 5 µL of 4×detection reagent at 8 nM (final concentration: 2 nM, Eu-anti-phospho-tyrosine antibody) was added to each well, followed by incubation at room temperature for 1 h. The plate was read using a PE Envision multi-functional microplate reader (excitation: 320 nm, emission: 665 nm), and IC$_{50}$ was calculated by four-parameter fitting.

The test results are shown in Table 1.

TABLE 1

| Compound number | BTK(WT) | EGFR | TEC | ITK |
| --- | --- | --- | --- | --- |
| | | IC$_{50}$ (nM) | | |
| I-1 | 52.1 | >1000 | 155.1 | >1000 |
| I-3 | 21.4 | 107.0 | 110.8 | >1000 |
| I-4 | 12.4 | >1000 | 25 | >1000 |
| I-7 | 9.7 | >1000 | NA | >1000 |

Note:
NA indicates not detected.

EXPERIMENTAL EXAMPLE 2: SCREENING FOR BTK (Y223) PHOSPHORYLATION INHIBITION ACTIVITY AT CELL LEVEL

20 µL of 30% hydrogen peroxide was added in 860 µL of double distilled water to prepare 200 mM hydrogen peroxide. PV (sodium pervanadate): 10 μL of 200 mmol/L sodium orthovanadate was reacted with 10 μL of 200 mmol/L hydrogen peroxide in 80 μL of RPMI 1640 complete medium at room temperature for 15 min, and the reaction solution was diluted with RPMI 1640 complete medium to 6 mM. It was prepared freshly prior to use. Ramos lymphoma cells in logarithmic growth phase were centrifuged at 1500 rpm for 3 min using a low-speed centrifuge, added with a proper amount of RPMI 1640 complete medium, resuspended and counted. A proper amount of corresponding culture medium was added to a proper amount of cell suspension to adjust the cell density to about 1-2×10E7 cells/mL. The cells at the above cell density were seeded in a 384-well plate at 20 μL/well, then 5 μL of compound was added to each well, and the plate was incubated for 1 h. 20 mM PV was diluted with RPMI 1640 complete medium to 6 mM (final concentration: 1 mM), added to wells at 5 μL/well according to the plate distribution, and incubated for 15-20 min. The blank group was wells seeded with cells, without compound and PV, and the control group was wells seeded with cells, without compound and with PV. 10 μL of lysis buffer (4×) containing blocking buffer was added immediately and incubated by shaking at room temperature for 30 min. After the mixture was mixed, 16 μL of lysate was transferred to another 384-well small-volume white plate. The plate was added with 4 μL of pre-mixed antibody (vol/vol) in assay buffer, covered, centrifuged to mix well, and incubated overnight at room temperature. The 665 nm/620 nm signal value was detected using a PE Envision multi-functional microplate reader, and $IC_{50}$ was calculated by four-parameter fitting. The test results are shown in Table 2.

TABLE 2

| Compound number | Ramos cells BTK (Y223) phosphorylation $IC_{50}$ (nM) |
|---|---|
| I-1 | 30 |
| I-3 | 25 |
| I-4 | 66 |
| I-7 | 52 |

EXPERIMENTAL EXAMPLE 3: IN VITRO METABOLIC STABILITY OF LIVER MICROSOME 3.1 Human Liver Microsome Assay 300 μL of final incubation system: 30 μL of human liver microsomes (protein concentration: 5 mg/mL, XENOTECH, USA), 30 μL of NADPH (10 mM)+$MgCl_2$ (5 mM), 3 μL of the substrate, i.e., the example compound (dissolved in 50% aqueous acetonitrile solution, 100 μM), and 237 μL of PBS buffer, wherein the proportion of the organic solvent (acetonitrile) was 0.5%. Each tube was added with 270 μL of a mixed solution of substrate and enzyme, and after being pre-incubated at 37° C. for 5 min, added with 30 μL of NADPH+$MgCl_2$. Then 50 μL of the mixture was taken at 0 min, 15 min, 30 min and 60 min, and added with 300 μL of diazepam glacial acetonitrile (20 ng/mL) containing an internal standard to quench the reaction. The reaction mixture was vortexed for 5 min, and centrifuged (13,000 rpm, 4° C.) for 10 min. 100 μL of supernatant was pipetted into a sample vial, from which 1 μL of supernatant was injected and analyzed by LC-MS/MS, and the residual percentage was calculated.

3.2 Mouse Liver Microsome Assay

300 μL of final incubation system: 30 μL of mouse liver microsomes (protein concentration: 5 mg/mL, XENOTECH, USA), 30 μL of NADPH (10 mM)+$MgCl_2$ (5 mM), 3 μL of the substrate, i.e., the example compound (dissolved in 50% aqueous acetonitrile solution, 100 μM), and 237 μL of PBS buffer, wherein the proportion of the organic solvent (acetonitrile) was 0.5%. Each tube was added with 270 μL of a mixed solution of substrate and enzyme, and after being pre-incubated at 37° C. for 5 min, added with 30 μL of NADPH+$MgCl_2$. Then 50 μL of the mixture was taken at 0 min, 15 min, 30 min and 60 min, and added with 300 μL of diazepam glacial acetonitrile (20 ng/mL) containing an internal standard to quench the reaction. The reaction mixture was vortexed for 5 min, and centrifuged (13,000 rpm, 4° C.) for 10 min. 100 μL of supernatant was pipetted into a sample vial, from which 1 μL of supernatant was injected and analyzed by LC-MS/MS, and the residual percentage was calculated.

3.3 Rat Liver Microsome Assay

300 μL of final incubation system: 30 μL of rat liver microsomes (protein concentration: 5 mg/mL, XENOTECH, USA), 30 μL of NADPH (10 mM)+$MgCl_2$ (5 mM), 3 μL of the substrate, i.e., the example compound (dissolved in 50% aqueous acetonitrile solution, 100 μM), and 237 μL of PBS buffer, wherein the proportion of the organic solvent (acetonitrile) was 0.5%. Each tube was added with 270 μL of a mixed solution of substrate and enzyme, and after being pre-incubated at 37° C. for 5 min, added with 30 μL of NADPH+$MgCl_2$. Then 50 μL of the mixture was taken at 0 min, 15 min, 30 min and 60 min, and added with 300 μL of diazepam glacial acetonitrile (20 ng/mL) containing an internal standard to quench the reaction. The reaction mixture was vortexed for 5 min, and centrifuged (13,000 rpm, 4° C.) for 10 min. 100 μL of supernatant was pipetted into a sample vial, from which 1 μL of supernatant was injected and analyzed by LC-MS/MS, and the remaining percentage was calculated.

The test results are shown in Table 3.

TABLE 3

| Compound number | Rat (RLM) | Mouse (MLM) | Human (HLM) |
|---|---|---|---|
| | Remaining % (T = 60 min) | | |
| I-1 | 30 | 90 | 89 |
| I-3 | 42 | 89 | 74 |
| I-4 | 26 | 32 | 15 |
| I-7 | 33.9 | 55.7 | 29.9 |

EXPERIMENTAL EXAMPLE 4: IN VIVO PHARMACOKINETIC ASSAY ON MOUSE

ICR mice weighing 18-22 g were randomly grouped into 9 mice in each group after being fed for 3-5 days, and administered intragastrically with related compound at a dose of 10 mg/kg, and injected intravenously with the test compound at a dose of 1 mg/kg, respectively. The test animals (ICR mice) were fasted for 12 h before administration and fed for 4 h after administration, and water was freely drunk before and after the experiment and during the experiment. After intragastric administration, 0.1 mL of the blood at the orbit was collected at 0.25 h (15 min), 0.5 h (30 min), 1 h, 2 h, 4 h, 6 h, 8 h, 10 h and 24 h, and after intravenous injection, 0.1 mL of the blood at the orbit was collected at 0.083 h (5 min), 0.167 h (10 min), 0.5 h (30 min), 1 h, 2 h, 6 h, 8 h, 10 h and 24 h. Each mouse was sampled at 3-4 time points, and 3 mice were sampled at each time point. Whole blood was collected and placed in centrifuge tubes containing EDTA-K2 and sodium fluoride, then transferred to a 4° C. centrifuge within 30 min and centrifuged at 4000 rpm for 10 min to separate the plasma. All plasma was collected and immediately stored at −20° C. for testing. 20 μL of a plasma test sample and a standard curve sample were pipetted into 300 μL of acetonitrile solution containing an internal standard (diazepam 20 mg/mL), and the mixture was shaken and mixed for 5 min, and centrifuged at 13,000 rpm for 10 min. 80 μL of supernatant was diluted with 80 μL of ultrapure water, and the mixture was mixed well, form which 1 μL of the sample was pipetted and analyzed by LC/MS/MS, and a chromatogram was recorded. Oral and intravenous exposure of the compounds disclosed herein was evaluated by pharmacokinetic experiments in mice and the results are shown in Table 4.

TABLE 4

| Parameters | Unit | I-1 (ig-10 mg/kg) | I-1 (iv-1 mg/kg) |
| --- | --- | --- | --- |
| AUC(0-t) | μg/L * h | 315 | 43.6 |
| AUC(0-∞) | μg/L * h | 315 | 43.6 |
| MRT(0-t) | h | 3.06 | 0.520 |
| t1/2z | h | 2.37 | 0.730 |
| Vz | L/kg | NA | 21.5 |
| CLz | L/h/kg | NA | 20.4 |
| Tmax | h | 0.250 | NA |
| Cmax | μg/L | 92.7 | NA |
| Absolute bioavailability F % | | | 72.4% |

Note:
ig: intragastric administration;
iv: intravenous injection;
MRT: mean residence time;
Vz: apparent volume of distribution;
CLz: clearance rate.

EXPERIMENTAL EXAMPLE 5: IN VIVO PHARMACODYNAMIC STUDY

OCI-LY10 cells were subcutaneously grafted (concentration: 1×10⁸/mL×0.1 mL/mice) in NOD-SCID mice at the right side armpit (the inoculated site was shaved upon grafting) under aseptic conditions. After subcutaneous grafting, the animals were grouped when the tumor volume reached about 100-300 mm³:

Model group: vehicle: 6 mice; I-1: 6 mice, 50 mg/kg, bid, i.g.; I-3: 6 mice, 50 mg/kg, bid, i.g.

The vehicle or compound was administered by intragastric administration at a volume of 10 mL/kg, twice daily, for 23 days. The tumor volume was measured 2-3 times per week, and the mice were weighed at the same time, with the data recorded. Animal behavior was observed daily. After all administration was completed, the animals were executed, stripped of tumors and weighed.

The tumor volume and the tumor growth inhibition were calculated using the following formulas:

Tumor volume(TV)=(Length×Width²)/2.

Tumor growth inhibition(TGI)=(1−tumor weight in treatment group/tumor weight in model group)× 100%.

TABLE 3

Therapeutic effect of the compounds on xenograft tumors of OCI-LY10 mice

| Group | d0 TV (mm³) Mean ± SD | d21 TV (mm³) Mean ± SD | d23 TV (mm³) Mean ± SD | TGI (%) |
| --- | --- | --- | --- | --- |
| Model group | 179 ± 35 | 1752 ± 210 | 2050 ± 248 | — |
| Group I-1 | 176 ± 35 | 742 ± 109 | 847 ± 189 | 79.4% |
| Group I-3 | 177 ± 16 | 645 ± 202 | 647 ± 343 | 84.1% |

** P < 0.01, compared to model group.

The invention claimed is:
1. A compound of formula (I), a stereoisomer thereof or a pharmaceutically acceptable salt thereof,

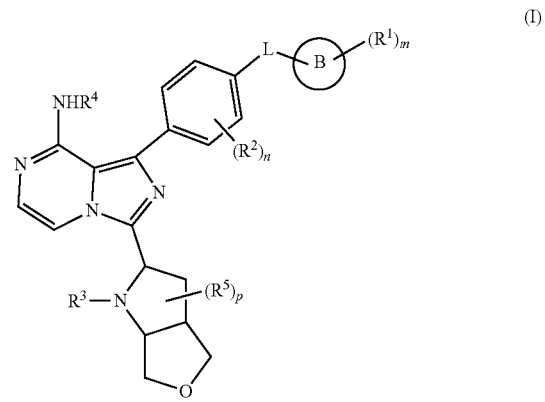

wherein,
ring B is selected from the group consisting of 5-10 membered heteroaryl and $C_{6\text{-}10}$ aryl;
$R^1$ is independently selected from the group consisting of halogen, —OH, —NH$_2$, cyano, $C_{1\text{-}6}$ alkyl and $C_{1\text{-}6}$ alkoxy, wherein $C_{1\text{-}6}$ alkyl or $C_{1\text{-}6}$ alkoxy is optionally substituted with halogen;
m is 0, 1, 2, 3 or 4;
L is selected from the group consisting of —C(O)NH—, —NHC(O)—, —O—, —NH—, —S—, —C(O)O—, —OC(O)—, —S(O)$_2$O— and —OS(O)$_2$—;
$R^2$ is independently selected from the group consisting of halogen, —OH, —NH$_2$, cyano, $C_{1\text{-}6}$ alkyl and $C_{1\text{-}6}$ alkoxy, wherein $C_{1\text{-}6}$ alkyl or $C_{1\text{-}6}$ alkoxy is optionally substituted with halogen;
n is 0, 1, 2, 3 or 4;
$R^3$ is selected from the group consisting of H, $R^aC(O)$—, $R^aS(O)_2$— and $R^a$—;
$R^5$ is independently selected from the group consisting of halogen, —OH, —NH$_2$, cyano, $C_{1\text{-}6}$ alkyl and $C_{1\text{-}6}$ alkoxy;
p is 0, 1, 2 or 3;
$R^4$ is selected from the group consisting of hydrogen, $R^aS(O)_2$—, $(R^aO)_2P(O)$— and $R^aC(O)$—;
wherein $R^a$ is independently selected from the group consisting of $C_{2\text{-}6}$ alkynyl, $C_{2\text{-}6}$ alkenyl, $C_{1\text{-}6}$ alkyl, $C_{3\text{-}6}$ cycloalkyl, ($C_{1\text{-}6}$ alkyl)NH—, ($C_{1\text{-}6}$ alkyl)$_2$N—, 3- to 6-membered heterocycloalkyl, 5- to 10-membered heteroaryl and $C_{6\text{-}10}$ aryl, wherein $R^a$ is optionally substituted with ($C_{1\text{-}6}$ alkyl)$_2$N—, ($C_{1\text{-}6}$ alkyl)NH—, hydroxy, amino, halogen or cyano.
2. The compound of formula (I), a stereoisomer thereof or a pharmaceutically acceptable salt thereof according to claim 1, wherein ring B is selected from the group consisting of 5- to 6-membered heteroaryl and phenyl.

3. The compound of formula (I), a stereoisomer thereof or a pharmaceutically acceptable salt thereof according to claim 1, wherein $R^1$ is independently selected from the group consisting of halogen, $C_{1-3}$ alkyl and $C_{1-3}$ alkoxy, wherein $C_{1-3}$ alkyl or $C_{1-3}$ alkoxy is optionally substituted with halogen.

4. The compound of formula (I), a stereoisomer thereof or a pharmaceutically acceptable salt thereof according to claim 1, wherein m is 0, 1 or 2.

5. The compound of formula (I), a stereoisomer thereof or a pharmaceutically acceptable salt thereof according to claim 1, wherein L is selected from the group consisting of —C(O)NH—, —NHC(O)—, —C(O)O— and —OC(O)—.

6. The compound of formula (I), a stereoisomer thereof or a pharmaceutically acceptable salt thereof according to claim 1, wherein $R^2$ is independently selected from the group consisting of halogen, —OH, —NH$_2$, $C_{1-3}$ alkyl and $C_{1-3}$ alkoxy.

7. The compound of formula (I), a stereoisomer thereof or a pharmaceutically acceptable salt thereof according to claim 1, wherein n is 0, 1 or 2.

8. The compound of formula (I), a stereoisomer thereof or a pharmaceutically acceptable salt thereof according to claim 1, wherein $R^3$ is selected from the group consisting of H, $R^aC(O)$— and $R^aS(O)_2$—.

9. The compound of formula (I), a stereoisomer thereof or a pharmaceutically acceptable salt thereof according claim 1, wherein $R^a$ is independently selected from the group consisting of $C_{2-6}$ alkynyl, $C_{2-6}$ alkenyl, $C_{1-6}$ alkyl, $C_{3-6}$ cycloalkyl, ($C_{1-6}$ alkyl)NH—, ($C_{1-6}$ alkyl)$_2$N—, 3- to 6-membered heterocycloalkyl, 5- to 10-membered heteroaryl and $C_{6-10}$ aryl, wherein $R^a$ is optionally substituted with ($C_{1-3}$ alkyl)$_2$N—, ($C_{1-3}$ alkyl)NH—, hydroxy or amino.

10. The compound of formula (I), a stereoisomer thereof or a pharmaceutically acceptable salt thereof according to claim 1, wherein $R^5$ is independently selected from the group consisting of F, —OH, —NH$_2$, methyl and methoxy, and p is 0, 1 or 2.

11. The compound of formula (I), a stereoisomer thereof or a pharmaceutically acceptable salt thereof according to claim 1, wherein $R^4$ is selected from the group consisting of hydrogen, $C_{3-6}$ cycloalkyl-S(O)$_2$— and ($C_{1-6}$ alkyl-O)$_2$P(O)—.

12. The compound of formula (I), a stereoisomer thereof or a pharmaceutically acceptable salt thereof according to claim 1, wherein the compound of formula (I) is selected from the group consisting of a compound of formula (II) and a compound of formula (III),

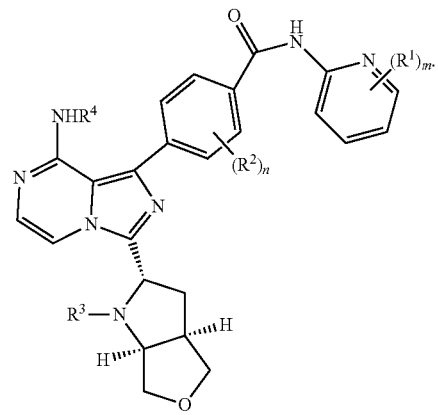

(II)

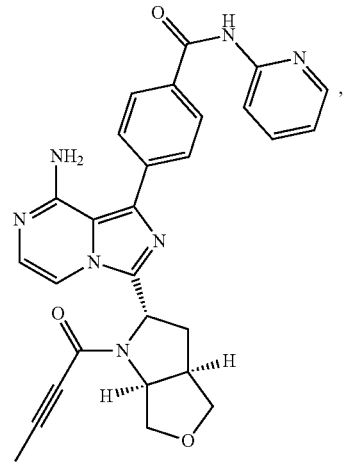

(III)

13. The compound of formula (I), a stereoisomer thereof or a pharmaceutically acceptable salt thereof according to claim 1, selected from the following compounds, a stereoisomer thereof or a pharmaceutically acceptable salt thereof:

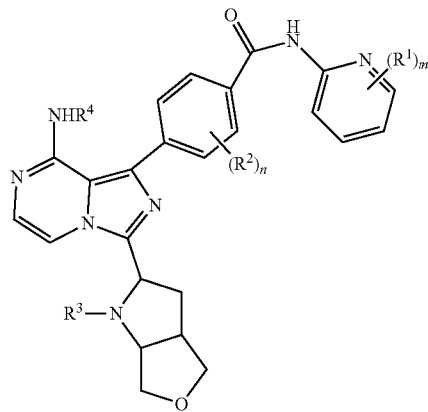

,

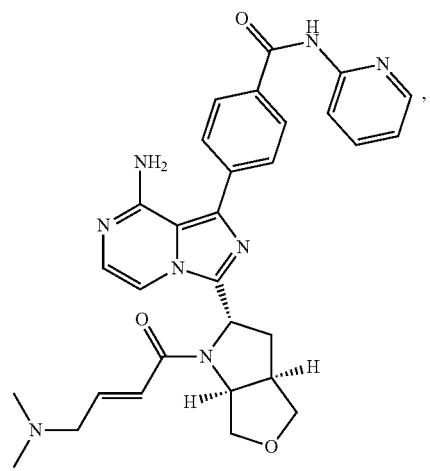

,

53
-continued
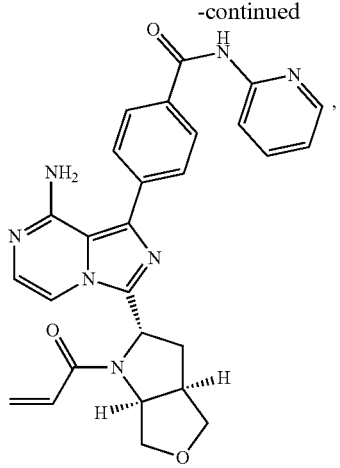
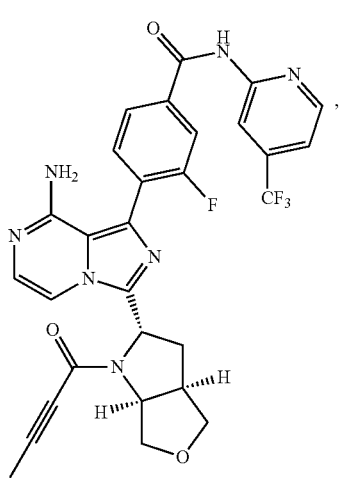
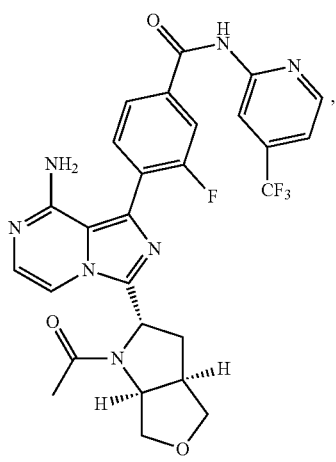
54
-continued
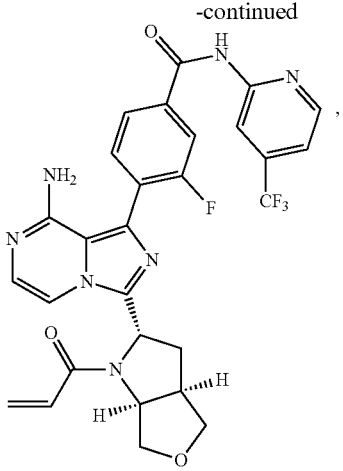
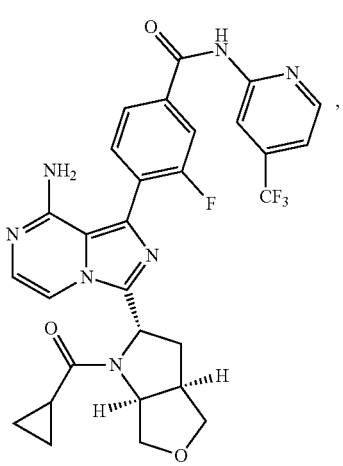
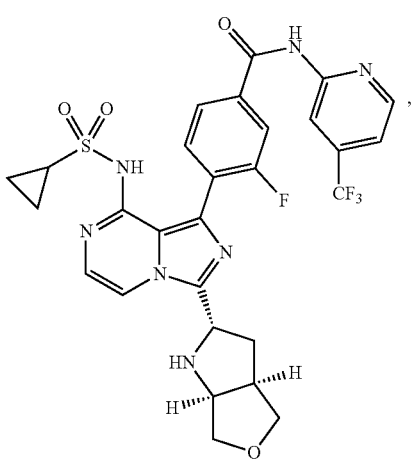

55
-continued
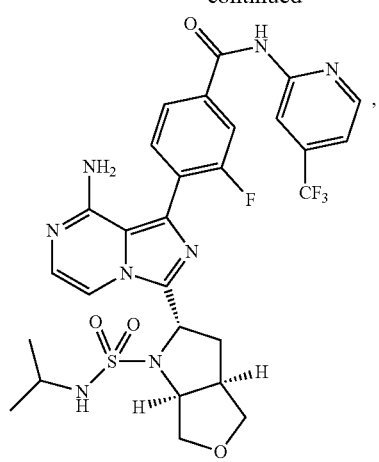
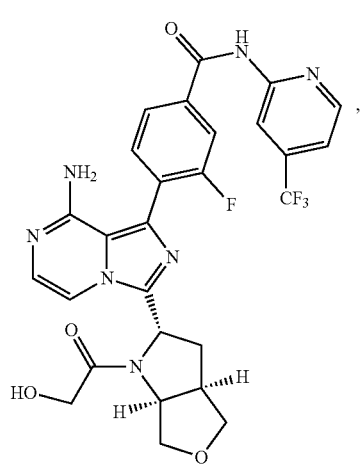
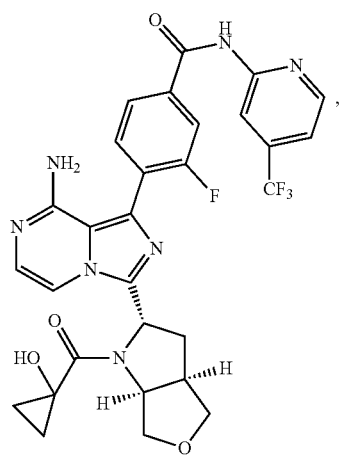
56
-continued
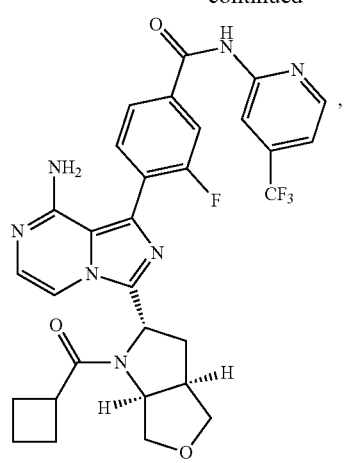
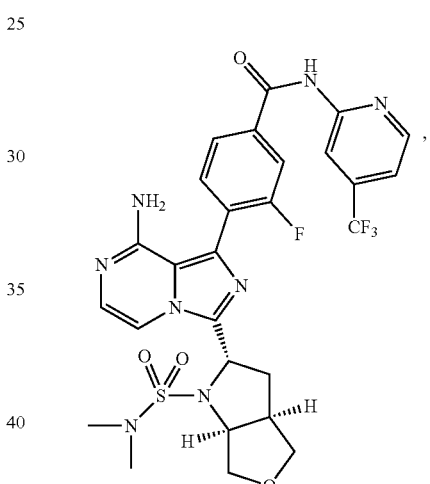
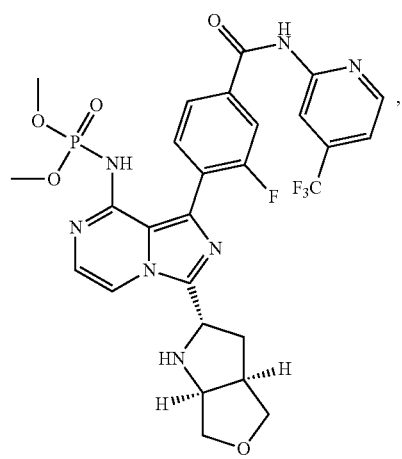

-continued

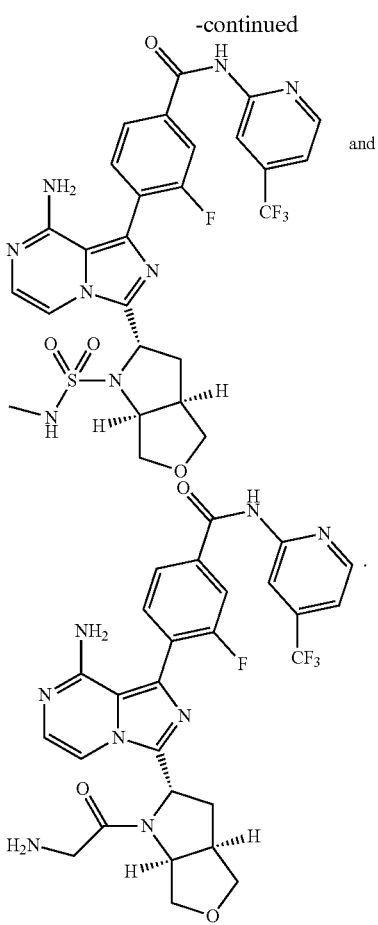

and

14. A pharmaceutical composition comprising the compound, a stereoisomer thereof or a pharmaceutically acceptable salt thereof according to claim 1.

15. A method for treating a BTK-related disease in a mammal, comprising administering to the mammal in need of such treatment a therapeutically effective amount of the compound, a stereoisomer thereof or a pharmaceutically acceptable salt thereof according to claim 1.

16. The method according to claim 15, wherein the BTK-related disease is selected from the group consisting of autoimmune diseases, inflammatory diseases and cancer; or the BTK-related disease is diffuse large B-cell lymphoma.

17. The compound of formula (I), a stereoisomer thereof or a pharmaceutically acceptable salt thereof according to claim 2, wherein ring B is pyridinyl.

18. The compound of formula (I), a stereoisomer thereof or a pharmaceutically acceptable salt thereof according to claim 3, wherein $R^1$ is trifluoromethyl.

19. The compound of formula (I), a stereoisomer thereof or a pharmaceutically acceptable salt thereof according to claim 9, wherein $R^a$ is independently selected from the group consisting of propynyl, $C_{2-3}$ alkenyl, methyl, cyclopropyl, cyclobutyl, $CH_3NH—$, $(CH_3)_2CHNH—$ and $(CH_3)_2N—$, wherein methyl, $C_{2-3}$ alkenyl and cyclopropyl are optionally substituted with $(CH_3)_2N—$, hydroxy or amino.

20. The compound of formula (I), a stereoisomer thereof or a pharmaceutically acceptable salt thereof according to claim 1, wherein $R^4$ is selected from the group consisting of hydrogen, cyclopropyl-$S(O)_2$— and $(CH_3O)_2$—P(O)—.

* * * * *